(12) United States Patent
Jackson et al.

(10) Patent No.: US 8,703,490 B2
(45) Date of Patent: Apr. 22, 2014

(54) COMPOSITIONS COMPRISING NANOMATERIALS AND METHOD FOR USING SUCH COMPOSITIONS FOR HISTOCHEMICAL PROCESSES

(75) Inventors: Merrill Jackson, Tucson, AZ (US); Michael Herman, Tucson, AZ (US); Grace Hoben, Marana, AZ (US); Noemi Sebastiao, Tucson, AZ (US); Scott Cockayne, Tucson, AZ (US); Heather Ferrea, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 425 days.

(21) Appl. No.: 12/995,790

(22) PCT Filed: Jun. 1, 2009

(86) PCT No.: PCT/US2009/045841
§ 371 (c)(1),
(2), (4) Date: Dec. 2, 2010

(87) PCT Pub. No.: WO2009/149013
PCT Pub. Date: Dec. 10, 2009

(65) Prior Publication Data
US 2011/0091897 A1 Apr. 21, 2011

Related U.S. Application Data

(60) Provisional application No. 61/131,205, filed on Jun. 5, 2008.

(51) Int. Cl.
*G01N 33/48* (2006.01)
(52) U.S. Cl.
USPC ........ 436/17; 436/10; 436/8; 436/18; 436/63; 435/40.5; 435/40.51; 435/40.52; 252/408.1
(58) Field of Classification Search
USPC .......... 436/10, 17, 8, 18, 63; 435/40.5, 40.51, 435/40.52; 252/408.1
See application file for complete search history.

(56) References Cited

U.S. PATENT DOCUMENTS

| 3,892,530 A | 7/1975 | Felix et al. |
| 4,230,683 A | 10/1980 | Decker et al. |

(Continued)

FOREIGN PATENT DOCUMENTS

| WO | WO 01/88089 | 11/2001 |
| WO | WO 2005/001889 | 6/2005 |

(Continued)

OTHER PUBLICATIONS

Oesterling et al., "Alumina nanoparticles induce expression of endothelial cell adhesion molecules", Toxicology Letters 178 (2008) 160-166.*

(Continued)

*Primary Examiner* — Monique Cole
(74) *Attorney, Agent, or Firm* — Klarquist Sparkman, LLP

(57) ABSTRACT

Histochemical process compositions comprising at least one nanoparticle in an amount effective to reduce or substantially eliminate the average number of spots per slide that result from a sample staining protocol are disclosed. Various nanoparticles, or combinations thereof, including metals, metal alloys, metal oxides, ceramics, functionalized metals or metalloids, and other miscellaneous nanoparticles, such as carbon nanoparticles and diamond nanoparticles, can be used. The nanoparticle concentration typically is from about 2 parts per million to about 20 parts per million. One embodiment of a disclosed method concerns applying a histochemical process composition to a sample, followed by performing a staining protocol on the sample. Particular embodiments concern dispensing a nanosolution onto a sample using an automated system, heating the sample, and performing a sample staining process.

63 Claims, 3 Drawing Sheets

(56) References Cited

U.S. PATENT DOCUMENTS

| | | |
|---|---|---|
| 4,425,427 A | 1/1984 | Luderer |
| 4,469,797 A | 9/1984 | Albarella |
| 4,490,473 A | 12/1984 | Brunhouse et al. |
| 4,495,296 A | 1/1985 | Neurath et al. |
| 4,879,224 A | 11/1989 | Wallner et al. |
| 5,198,537 A | 3/1993 | Huber et al. |
| 5,225,325 A | 7/1993 | Miller et al. |
| 5,322,771 A | 6/1994 | Rybski et al. |
| 5,350,686 A | 9/1994 | Jhingan |
| 5,403,747 A | 4/1995 | Akins et al. |
| 5,418,138 A | 5/1995 | Miller et al. |
| 5,447,841 A | 9/1995 | Gray et al. |
| 5,487,975 A | 1/1996 | Miller et al. |
| 5,643,761 A | 7/1997 | Fisher et al. |
| 5,648,211 A | 7/1997 | Fraiser et al. |
| 5,648,245 A | 7/1997 | Fire et al. |
| 5,650,327 A | 7/1997 | Copeland et al. |
| 5,654,200 A | 8/1997 | Copeland et al. |
| 5,661,040 A | 8/1997 | Huff et al. |
| 5,679,582 A | 10/1997 | Bowie et al. |
| 5,684,142 A | 11/1997 | Mishra et al. |
| 5,731,171 A | 3/1998 | Bohlander |
| 5,756,696 A | 5/1998 | Gray et al. |
| 5,759,808 A | 6/1998 | Casterman et al. |
| 5,800,988 A | 9/1998 | Casterman et al. |
| 5,840,526 A | 11/1998 | Casterman et al. |
| 5,874,541 A | 2/1999 | Casterman et al. |
| 5,883,081 A | 3/1999 | Kraus et al. |
| 5,994,071 A | 11/1999 | Ross et al. |
| 6,005,079 A | 12/1999 | Casterman et al. |
| 6,015,695 A | 1/2000 | Casterman et al. |
| 6,057,099 A | 5/2000 | Nathan et al. |
| 6,124,120 A | 9/2000 | Lizardi |
| 6,180,349 B1 | 1/2001 | Ginzinger et al. |
| 6,194,388 B1 | 2/2001 | Krieg et al. |
| 6,207,299 B1 | 3/2001 | Krauth et al. |
| 6,207,646 B1 | 3/2001 | Krieg et al. |
| 6,214,806 B1 | 4/2001 | Krieg et al. |
| 6,218,152 B1 | 4/2001 | Auerbach |
| 6,218,371 B1 | 4/2001 | Krieg et al. |
| 6,235,480 B1 | 5/2001 | Shultz et al. |
| 6,239,116 B1 | 5/2001 | Krieg et al. |
| 6,280,929 B1 | 8/2001 | Gray et al. |
| 6,280,949 B1 | 8/2001 | Lizardi |
| 6,291,187 B1 | 9/2001 | Kingsmore et al. |
| 6,296,809 B1 | 10/2001 | Richards et al. |
| 6,322,901 B1 | 11/2001 | Bawendi et al. |
| 6,323,009 B1 | 11/2001 | Lasken et al. |
| 6,339,068 B1 | 1/2002 | Krieg et al. |
| 6,344,337 B1 | 2/2002 | Mansfield et al. |
| 6,352,861 B1 | 3/2002 | Copeland et al. |
| 6,358,682 B1 | 3/2002 | Jaffee et al. |
| 6,406,705 B1 | 6/2002 | Davis et al. |
| 6,414,133 B1 | 7/2002 | Dietz-Band et al. |
| 6,429,199 B1 | 8/2002 | Krieg et al. |
| 6,432,320 B1 | 8/2002 | Bonsignore et al. |
| 6,447,692 B1 | 9/2002 | Momoda et al. |
| 6,495,324 B1 | 12/2002 | Mirkin et al. |
| 6,506,564 B1 | 1/2003 | Mirkin et al. |
| 6,544,798 B1 | 4/2003 | Christensen et al. |
| 6,569,621 B1 | 5/2003 | Cremer et al. |
| 6,576,291 B2 | 6/2003 | Bawendi et al. |
| 6,582,921 B2 | 6/2003 | Mirkin et al. |
| 6,592,844 B2 | 7/2003 | Coombes et al. |
| 6,607,877 B1 | 8/2003 | Gray et al. |
| 6,617,137 B2 | 9/2003 | Dean et al. |
| 6,649,138 B2 | 11/2003 | Adams et al. |
| 6,656,685 B2 | 12/2003 | Utermohlen et al. |
| 6,673,214 B1 | 1/2004 | Marchitto et al. |
| 6,682,596 B2 | 1/2004 | Zehnder et al. |
| 6,695,974 B2 | 2/2004 | Withers et al. |
| 6,696,304 B1 | 2/2004 | Davies |
| 6,699,973 B1 | 3/2004 | O'Mahony et al. |
| 6,750,016 B2 | 6/2004 | Mirkin et al. |
| 6,767,702 B2 | 7/2004 | Mirkin et al. |
| 6,797,474 B2 | 9/2004 | Lizardi |
| 6,815,064 B2 | 11/2004 | Treadway et al. |
| 6,827,901 B2 | 12/2004 | Copeland et al. |
| 6,828,097 B1 | 12/2004 | Knoll et al. |
| 6,855,552 B2 | 2/2005 | Towne et al. |
| 6,921,496 B2 | 7/2005 | Anderson et al. |
| 6,933,117 B2 | 8/2005 | Wolf et al. |
| 6,942,970 B2 | 9/2005 | Isola et al. |
| 6,943,029 B2 | 9/2005 | Copeland et al. |
| 6,944,333 B2 | 9/2005 | Douglass |
| 6,962,789 B2 | 11/2005 | Bacus |
| 6,977,148 B2 | 12/2005 | Dean et al. |
| 7,014,997 B2 | 3/2006 | Knoll et al. |
| 7,045,504 B2 | 5/2006 | Wilhelm et al. |
| 7,056,471 B1 | 6/2006 | Han et al. |
| 7,067,325 B2 | 6/2006 | Christensen et al. |
| 7,087,379 B2 | 8/2006 | Light |
| 7,104,313 B2 | 9/2006 | Pokharna et al. |
| 7,200,252 B2 | 4/2007 | Douglass |
| 7,250,254 B2 | 7/2007 | Dietz-Band et al. |
| 7,285,289 B2 | 10/2007 | Nagy et al. |
| 7,292,718 B2 | 11/2007 | Douglass |
| 7,300,748 B2 | 11/2007 | Fischer et al. |
| 7,358,041 B2 | 4/2008 | Short et al. |
| 7,541,455 B2 | 6/2009 | Bieniarz et al. |
| 7,682,789 B2 | 3/2010 | Chen et al. |
| 7,695,929 B2 | 4/2010 | Kosmeder et al. |
| 2001/0051342 A1 | 12/2001 | Farrell |
| 2002/0019001 A1 | 2/2002 | Light |
| 2002/0117659 A1 | 8/2002 | Lieber et al. |
| 2003/0003537 A1 | 1/2003 | Fischer et al. |
| 2003/0008414 A1 | 1/2003 | Nie et al. |
| 2003/0022166 A1 | 1/2003 | Collins et al. |
| 2003/0022243 A1 | 1/2003 | Kondejewski et al. |
| 2003/0059790 A1 | 3/2003 | Jaffee et al. |
| 2003/0066998 A1 | 4/2003 | Lee |
| 2003/0122630 A1 | 7/2003 | Fallisgaard et al. |
| 2003/0165485 A1 | 9/2003 | Bertilsson et al. |
| 2004/0052685 A1 | 3/2004 | Richards |
| 2004/0057958 A1 | 3/2004 | Waggoner et al. |
| 2004/0077844 A1 | 4/2004 | Jacobson et al. |
| 2004/0101822 A1 | 5/2004 | Wiesner et al. |
| 2004/0115727 A1 | 6/2004 | Steward et al. |
| 2004/0161742 A1 | 8/2004 | Dean et al. |
| 2004/0209303 A1 | 10/2004 | Martin et al. |
| 2004/0214245 A1 | 10/2004 | Schmitt et al. |
| 2004/0229300 A1 | 11/2004 | Frederickson |
| 2004/0248151 A1 | 12/2004 | Bacus et al. |
| 2004/0253603 A1 | 12/2004 | Utermohlen et al. |
| 2004/0265897 A1 | 12/2004 | Lizardi |
| 2004/0265922 A1 | 12/2004 | Bieniarz et al. |
| 2005/0012182 A1 | 1/2005 | Jang et al. |
| 2005/0014133 A1 | 1/2005 | Light et al. |
| 2005/0019901 A1 | 1/2005 | Matveeva et al. |
| 2005/0048498 A1 | 3/2005 | Woudenberg et al. |
| 2005/0054578 A1 | 3/2005 | Sandberg et al. |
| 2005/0064488 A1 | 3/2005 | Huh et al. |
| 2005/0074890 A1 | 4/2005 | Lemme et al. |
| 2005/0106639 A1 | 5/2005 | Bacus et al. |
| 2005/0112636 A1 | 5/2005 | Hurt et al. |
| 2005/0118725 A1 | 6/2005 | Towne et al. |
| 2005/0158770 A1 | 7/2005 | Bieniarz et al. |
| 2005/0159432 A1 | 7/2005 | Shepard et al. |
| 2005/0164213 A1 | 7/2005 | Tabor et al. |
| 2005/0181394 A1 | 8/2005 | Steemers et al. |
| 2005/0272032 A1 | 12/2005 | Ji |
| 2006/0110744 A1 | 5/2006 | Sampas et al. |
| 2006/0148124 A1 | 7/2006 | Wilson |
| 2006/0160116 A1 | 7/2006 | Christian et al. |
| 2006/0192283 A1 | 8/2006 | Benson |
| 2006/0246524 A1 | 11/2006 | Bauer et al. |
| 2006/0275784 A1 | 12/2006 | Light et al. |
| 2007/0057263 A1 | 3/2007 | Kahen |
| 2007/0099283 A1 | 5/2007 | Mueller et al. |
| 2007/0117153 A1 | 5/2007 | Bieniarz et al. |
| 2007/0274996 A1 | 11/2007 | Carter et al. |

(56) References Cited

U.S. PATENT DOCUMENTS

2008/0057513 A1 3/2008 Farrell
2010/0151489 A1 6/2010 Chen et al.

FOREIGN PATENT DOCUMENTS

WO WO 2007/079128 7/2007
WO WO 2008/028156 3/2008

OTHER PUBLICATIONS

Gerhardt et al., "Titanium dioxide (TiO2) nanoparticles filled poly (D,L lactid acid) (PDLLA) matrix composites for bone tissue engineering", J. Mater. Sci.: Mater Med (2007) 18:1287-1298.*
Baglin et al., "A Review of Natural and Modified Betulinic, Ursolic and Echinocystic Acid Derivatives as Potential Antineoplastic Agents," *Mini Review in Medicinal Chemistry* 3:540-556, 2003.
Baltina et al., "Chemical Modification of Glycyrrhizic Acid as a Route to new Bioactive Compounds for Medicine," *Current Medicinal Chemistry* 10:155-171, 2003.
Bang et al., "Boiling heat transfer performance and phenomena of $Al_2O_3$-water nano-fluids from a plain surface in a pool," *International Journal of Heat and Mass Transfer* 48:2407-2419, 2005.
Bellon, "Quantitation and specific detection of collagenous proteins using an enzyme-linked immunosoret assay and an immunoblotting for cyanogens bromide peptides," *Analtyic Biochemistry* 150:188-202, 1985.
Böhlen et al., "Fluorometric Assay of Proteins in the Nanogram Range," *Archives of Biochemistry and Biophysics* 155:213-220, 1973.
Buongiorno et al., "Use of Nanofluids for Enhanced Economics and Safety of Nuclear Reactors," *COE-INES International Symposium*, 14 pages, Yokahama, Nov. 26-30, 2006.
Chan et al., "Quantum Dot Bioconjugates for Ultrasensitive Nonisotopic Detection," *Science* 281:2016-2018, Sep. 25, 1998.
Connolly and Hill, "Triterpenoids," *Nat. Prod. Rep.* 19:494-513, 2002.
Crombie and Whiting, "Biosynthesis of Rotenoids Group of Natural Products: Application of Isotope Methodology," *Phytochemistry* 49:1479-1507, 1998.
Das et al., "Pool boiling characteristics of nano-fluids," *International Journal of Heat and Mass Transfer* 46:851-862, 2003.
Demers et al., "A Fluorescence-based method for determining the surface coverage and hybridization efficiency of thiol-capped oligonucleotides bound to gold thin films and nanoparticles," *Analytical Chemistry* 72:5535-5541, 2000.
Desbene et al., "Drugs that Inhibit Tubulin Polymerization: The Particular Case of Podophyllotoxin and Analogues," *Current Medicinal Chemistry—Anti-Cancer Agents* 2:71-90, 2002.
Devi et al., "Antibodies to poly[(2→8)-α-N-Acetylneuraminic acid] and poly[(2→9)-α-N-Acetylneuraminic acid] are Elicited by Immunization of Mice with *Escherichia coli* K92 Conjugates: Potential Vaccines for Groups B and C Meningococci and *E. coli* K1," *PNAS* 88:7175-7179, 1991.
Dintzis et al., "Molecular Determinants of Immunogenicity: The Immunon Model of Immune Response," *Proc. Natl. Acad. Sci. USA* 73(10):3671-3675, Oct. 1976.
Dong et al., "Study of Fluorescence Quenching and Dialysis Process of CdTe Quantum Dots, Using Ensemble Techniques and Fluorescence Correlation Spectroscopy," *J. Phys. Chem. B* 110:10069-10075, 2006.
Draper et al., "Attachment of reporter groups to specific, selected cytidine residues in RNA using a bisulfate-catalyzed transamination reaction," *Nucleic Acids Research* 12(2):989-1002, 1984.
Dubertret et al., "In vivo imaging of quantum dots encapsulated in phospholipid micelles," *Science* 298:1759-1762, 2002.

Dubois et al., "A Versatile Strategy for Quantum Dot Ligand Exhange," *Journal of the American Chemical Society* 129(3):482-483, 2007.
Dyal et al., "Activity of *Candida rugosa* lipase Immobilized on γ-$Fe_2O_3$ Magnetic Nanoparticles," *Journal of the American Chemical Society* 125:1684-1685, 2003.
Eastman et al., "Anomalously increased effective thermal conductivities of ethylene glycol-based nanofluids containing copper nanoparticles," *Applied Physics Letters* 78(6):718-720, Feb. 5, 2001.
Fang et al., "Cube Resin Insecticide: Identification and Biological Activity of 29 Rotenoid Constituents," *J. Agric. Food. Chem.* 47:2130-2136, 1999.
Fattom et al., "Serum antibody response in adult volunteers elicited by injection of *Streptococcus pneumoniae* type 12F polysaccharide alone or conjugated to diphtheria toxoid," *Infect. Immun.* 582309-2312, 1990.
"Fluorescent Labels for Antibodies and Molecular Probes," http://hmds.org.uk/fluorochrome.html, HMDS, 8 pages, Nov. 11, 2003.
Gerardi, "Experimental Study of Boiling Crisis Phenomena in Nanofluids," *National Nuclear Society Student Conference*, 19 pages, Mar. 30, 2007.
Gilham, "An addition reaction specific to uridine and suanosine nucleotides and its application to the modification of ribonuclease action," *J. Am. Chem. Soc.* 84:687-688, 1962.
Gordaliza et al., "Podophyllotoxin: Distribution, Sources, Applications and New Cytotoxic Derivatives," *Toxicon* 44:441-459, 2004.
Han et al., "Quantum-dot-tagged microbeads for multiplexed optical coding of biomolecules," *Nature Technology* 19:631-635, Jul. 2001.
Heafey et al., "Comparative study of the quenching of core and core-shell CdSe quantum dots by binding and non-binding nitroxides," *Photochemical and Photobiological Sciences* 6:580-584, 2007.
Heid et al., "Real time Quantitative PCR," *Genome Research* 6:986-994, 1996.
Hickman et al., "Combining Spontaneous Molecular Assembly with Microfabrication to Pattern Surfaces: Selective Binding of Isonitriles to Platinum Microwires and Characterization by Electrochemistry and Surface Spectroscopy," *Journal of the American Chemical Society* 111:7271-7272, 1989.
Hill et al., "The bio-barcode assay for the detection of protein and nucleic acid targets using DTT-induced ligand exchange," *Nature Protocols* 1(1):324-336, 2006.
Iijima et al., "Dispersion Behavior of Barium Titanate Nanoparticles Prepared by Using Various Polycarboxylic Dispersants," *Journal of the American Chemical Society* 90(9):2741-2746, 2007.
Jackson et al., "Characteristics of Nucleate Boiling with Gold Nanoparticles in Water," *Proceedings of IMECE 2006*, 2006 ASME International Mechanical Engineering Congress and Exposition, pp. 385-390, Chicago, Illinois, Nov. 5-10, 2006.
Jaiswal et al., "Long-term multiple color imaging of live cells using quantum dot bioconjugates," *Nature Biotechnol.* 21:47-51, 2003.
Kats et al., "Spectroscopic determination of protein concentrations from proteinase K digests," *Analytical Biochemistry* 307:212-218, 2002.
Kim et al., "A real-time PCR-based method for determining the surface coverage of thiol-capped oligonucleotides bound onto gold nanoparticles," *Nucleic Acids Research* 34(7):e54, 2006.
Kim et al., "Effects of nanoparticle deposition on surface wettability influencing boiling heat transfer in nanofluids," *Applied Physics Letters* 89(153107):1-3, 2006.
Kim et al., "Experimental studies on CHF characteristics of nano-fluids at pool boiling," *International Journal of Multiphase Flow* 33:391-706, 2007.
Kim et al., "Surface wettability change during pool boiling of nanofluids and its effect on critical heat flux," *International Journal of Heat and Mass Transfer* 50:4105-4116, 2007.
Koh et al., "Magnetic Iron Oxide Nanoparticles for Biorecognition: Evaluation of surface coverage and activity," *Journal of Physical Chemistry* 110:1553-1448, 2006.
Layne, "Spectrophotometric and turbidimetric methods for measuring proteins," *Methods in Enzymology* 3:447-454, 1957.

(56) References Cited

OTHER PUBLICATIONS

Lee et al., "Suppression of Reaginic Antibody Formulation: III. Relationship Between Immunogenicity and Tolerogenicity of Hapten-Carrier Conjugates," *J. Immunol.* 116:1171-1718, 1976.

Link et al., "Size and Temperature Dependence of the Plasmon Absorption of Colloidal Gold Nanoparticles," *Journal of Physical Chemistry B* 103(21):4212-4217, 1999.

Masuda et al., "New biotinylating reagent utilizing carbodiimide function," *Nucleic Acids Symp. Ser.* 34:69-70, 1995.

Masui et al., "Synthesis of cerium oxide nanoparticles by hydrothermal crystallization with citric acid," *Journal of Materials Science Letters* 21:489-491, 2002.

Matteucci et al., "Synthesis of Deoxyoligonucleotides on a Polymer Support," *Journal of the American Chemical Society* 103:3185-3191, 1981.

Meresse et al., "Etoposide: Discovery and Medicinal Chemistry," *Current Medicinal Chemistry* 11:2443-2466, 2004.

Metz and Brown, "The investigation of nucleic acid secondary structure by means of chemical modification with a carbodiimide reagent. I. The reaction between N-cyclohexyl-N'β-(4-methylmorphilinium)ethylcarbodiimide and model nucleosides," *Biochem.* 8(6):2312-2328, 1969.

Milanova et al., "Role of ions in pool boiling heat transfer of pure and silica nanofluids," *Applied Physics Letters* 87(233107):1-3, 2005.

Moreno et al., "Pool Boiling Heat Transfer of Alumina-Water, Zinc Oxide-Water and Alumina-Water+Ethylene Glycol Nanofluids," *Proceedings of HT2005, 2005 ASME Summer Heat Transfer Conference*, pp. 625-632, San Francisco, California, Jul. 17-22, 2005.

Mucic et al., "Synthesis and characterization of DNA with ferrocenyl groups attached to their 5'-termini: electrochemical characterization of a redox-active nucleotide monolayer," *Chem. Comm.*, pp. 555-557, 1996.

Mukumoto et al., "Investigation of ferrocenyl carbodiimide (FCDI) in the modification reaction of nucleic acids," *Nucleic Acids Sump. Ser. (Oxf)* 49:231-232, 2005.

"Note 7.1—Product Highlight: Guide to Labeling Antibodies with Alexa Fluor Dyes," http://probes.invitrogen.com/handbook/boxes/2020.html, Invitrogen, pp. 6-9, Apr. 2, 2006.

Otsuka et al., "Quantitative and Reversible Lectin-Induced Association of Gold Nanoparticles Modified with α-Lactosyl-ω-mercapto-poly(ethylene glycol)," *Journal of the American Chemical Society* 123(34):8226-8230, 2001.

Pathak et al., "Hydroxylated quantum dots as luminescent probes for in situ hybridization," *Journal of the American Chemical Society* 123:4103-4104, 2001.

Pavliakova et al., "Treatment with Succinic Anhydride Improves the Immunogenicity of *Shigella flexneri* Type 2a O-specific Polysaccharide-Protein Conjugates in Mice," *Infect. Immun.* 68:2161-2166, 1999.

Perkins, "Protein volumes and hydration effects," *Eur. J. Biochem.* 157:169-180, 1986.

Pozsgay et al., "Protein conjugates of synthetic saccharides elicit higher levels of serum IgG lipopolysaccharide antibodies in mice than do those of the O-specific polysaccharide from *Shigella dysenteriae* type 1," *PNAS* 96:5194-5197, 1999.

Pujol et al., "Synthesis of Biological Activity of New Class of Dioxygenated Anticancer Agents," *Current Medicinal Chemistry—Anti-Cancer Agents* 5:215-237, 2005.

Rigby et al., "Labeling deoxyribonucleic acid to high specific activity in vitro by nick translation with DNA polymerase 1," *Journal of Molecular Biology* 113:237-251, 1977.

Rockenberger et al., "A New Nonhydrolytic Single-Precursor Approach in Surfactant-Capped Nanocrystals of Transition Metal Oxides," *Journal of the American Chemical Society* 121(49):11595-11596, 1999.

Santra et al., "Rapid and effective labeling of brain tissue using TAT-conjugated CdS:Mn/ZnS quantum dots," *Chemical Communications*, pp. 3144-3146, 2005.

Setzer and Setzer, "Plant-Derived Triterpenoids as Potential Antineoplastic Agents," *Mini Reviews in Medicinal Chemistry* 3:540-556, 2003.

Simonian, "Spectrophotometric Determination of Protein Concentration," *Current Protocols in Food Analytical Chemistry* B1.3.1-B.13.7, 2002.

Singh et al., "Advances in Vaccine Adjuvants," *Nat. Biotechnol.* 17:1075-1081, 1999.

Sun et al., "Shape-Controlled Synthesis of Gold and Silver Nanoparticles," *Science* 398:2176-2179, Dec. 13, 2002.

Szu et al., "Vi Capsular Polysaccharide-Protein Conjugates for Prevention of Typhoid Fever," *Journal of Experimental Medicine* 166:1510-1524, 1987.

Szu et al., "Relation between Structure and Immunologic Properties of the Vi Capsular Polysaccharide," *Infect. Immun.* 59:4555-4561, 1987.

Thanh et al., "Development of an Aggregation-Based Immunoassay for Anti-Protein A Using Gold Nanoparticles," *Analytical Chemistry* 74(7):1624-1628, 2002.

Theofanous et al., "The boiling crisis phenomenon—Part I: nucleation and nucleate boiling heat transfer," *Experimental Thermal and Fluid Science* 26:775-792, 2002.

Theofanous et al., "The boiling crisis phenomenon—Part II: dryout dynamics and burnout," *Experimental Thermal and Fluid Science* 26:793-810, 2002.

Tsugita et al., "A rapid vapor-phase acid (hydrochloric acid and trifluoroacetic acid) hydrolysis of peptide and protein," *Journal of Biochemistry* 102:1593-1597, 1987.

Udenfriend et al., "Fluorescamine: A Reagent for Assay of Amino Acids, Peptides, Proteins and Primary Amines in the Picomole Range," *Science* 178:870-872, Nov. 24, 1972.

Vassallo et al., "Pool boiling heat transfer experiments in silica-water nano-fluids," *International Journal of Heat and Mass Transfer* 47:407-411, 2004.

Wang et al., "Effect of Surface Wettability on Active Nucleation Site Density During Pool Boiling of Water on a Vertical Surface," *Journal of Heat Transfer* 115:659-669, Aug. 1993.

Wen et al., "Experimental investigation into the pool boiling heat transfer of aqueous based γ-alumina nanofluids," *Journal of Nanoparticle Research* 7:265-274, 2005.

Woehrle et al., "Thiol-functionalized 1.5-nm gold nanoparticles through ligand exchange reactions: Scope and mechanism of ligand exchange," *Journal of the American Chemical Society* 127(7):2172-2183, 2005.

Wu et al., "Immunofluorescent labeling of cancer marker Her2 and other cellular targets with semiconductor quantum dots," *Nature Biotech.* 21:41-46, 2003.

Xu et al., "Immunoassay using probe-labelling immungold nanoparticles with silver staining enhancement via surface-enhanced Raman scattering," *Analyst* 129:63-68, 2004.

Yi et al., "Water-Soluble $NaYF_4$:Yb,Er(Tm)/$NaYF_4$/Polymer Core/Shell/Shell Nanoparticles with Significant Enhancement of Upconversion Fluorescence," *Chemistry of Materials* 19:341-343, 2007.

You et al., "Effect of nanoparticles on critical heat flux of water in pool boiling heat transfer," *Applied Physics Letters* 83(16):3374-3376, Oct. 20, 2003.

You et al., "Podophyllotoxin Derivatives: Current Synthetic Approaches for New Anticancer Agents," *Current Pharmaceutical Design* 11:1695-1717, 2005.

Yu et al., "Water-soluble quantum dots for biomedical applications," *Biochemical and Biophysical Research Communications* 348:781-786, 2006.

International Search Report dated Aug. 24, 2005, from International Application No. PCT/US2004/042969.

International Search Report dated Sep. 23, 2008, from International Application No. PCT/US2007/023140.

International Search Report dated Dec. 16, 2009, from International Application No. PCT/US2009/045841.

(56) References Cited

OTHER PUBLICATIONS

Office action dated Sep. 17, 2008, from U.S. Appl. No. 11/800,360.
Office action dated Apr. 2, 2009, from U.S. Appl. No. 11/800,360.
Office action dated Dec. 19, 2008, from U.S. Appl. No. 11/982,627.
Office action dated Jul. 24, 2009, from U.S. Appl. No. 11/982,627.
Office action dated Aug. 17, 2010, from U.S. Appl. No. 12/658,092.

Mühlfeld et al., "Visualization and quantitative analysis of nanoparticles in the respiratory tract by transmission electron microscopy," *Particle and Fibre Toxicology* vol. 4, No. 11, 17 pages, Nov. 12, 2007.

Smith et al., "Multicolor quantum dots for molecular diagnostics of cancer," *Expert Rev. Mol. Diagn.* 6(2):231-244, 2006.

* cited by examiner

COMPOSITIONS COMPRISING NANOMATERIALS AND METHOD FOR USING SUCH COMPOSITIONS FOR HISTOCHEMICAL PROCESSES

CROSS REFERENCE TO RELATED APPLICATIONS

This is the U.S. National Stage of International Application No. PCT/US2009/045841, filed Jun. 1, 2009, which was published in English under PCT Article 21(2), which in turn claims the benefit of the earlier filing date of U.S. Provisional Application No. 61/131,205 filed Jun. 5, 2008. The provisional application is incorporated herein in its entirety.

FIELD

The present invention concerns compositions comprising nanomaterials, particularly nanoparticles, where the compositions are particularly useful for histochemical processes, and embodiments of a method for using such compositions for performing histochemical processes.

BACKGROUND

I. Histochemical Processes

Histology is the microscopic examination of tissue samples to identify structural and other changes in cells, tissues and organs. Histochemical processes include examining biological molecules that cause or are otherwise associated with disease to elucidate information about patient diagnosis, prognosis, and treatment options, and generally are divided into two main areas: (i) analysis of DNA, mRNA, and proteins in intact cells (in-situ); and (ii) analysis of these biological materials after they have been extracted from tissues. The first category allows a pathologist to study the histopathologic architecture or morphology of the tissue specimen while nucleic acids or proteins are being assayed. These techniques include immunohistochemistry (IHC) for analyzing proteins, in-situ hybridization (ISH) for analyzing nucleic acids, histochemistry (HC) for analyzing carbohydrates, and enzyme histochemistry (EHC) for enzyme chemistry.

IHC uses antibodies to bind specifically to unique epitopes, such as epitopes found on proteins that may be expressed only in certain types of diseased cellular tissue, and more particularly involves selectively detecting such epitopes in a tissue section or cells (e.g. blood or bone marrow) mounted on a glass slide. Typical IHC process steps include pretreating the tissue section to remove embedding paraffin and to reduce non-specific binding, retrieval of antigens masked by cross-linking of proteins by chemical fixatives, antibody treatment and incubation, enzyme labeled secondary antibody treatment and incubation, substrate reaction with the enzyme to produce a fluorophore or chromophore highlighting areas of the tissue section having epitopes bound with the antibody, counterstaining, and the like. In particular, antigen retrieval typically is performed at elevated temperatures.

ISH uses nucleic acid probes to detect target nucleic acid sequences in a sample. For example, ISH can be used to detect oncogenes, such as Her2, EGFR and TOPIIA gene sequences. ISH can be used to detect a genetic abnormality or condition, such as amplification of cancer causing genes specifically in cells that, when viewed under a microscope, morphologically appear to be malignant. ISH also is useful for diagnosing infectious diseases. Typical ISH process steps include pretreating the tissue section to remove embedding paraffin and to reduce non-specific binding, retrieval of target nucleic acid sequences, hybridization of nucleic acid probes to target sequences, and detection of the probe bound to its target. In particular, target retrieval and probe hybridization steps are performed at elevated temperatures.

II. Automated Systems

Automated sample staining systems have been developed to reduce human labor, error rate and expense. Representative microprocessor-controlled systems include a slide carousel that is rotated by a stepper motor to serially place sample slides adjacent dispensers to receive processing reagents or compositions for performing histochemical processes. Bar codes on the slides and dispensers allow the computer to control different treatment regimens for various tissue samples. These staining systems also include a heat source to heat the samples for steps requiring elevated temperatures, or steps that are facilitated by temperatures greater than ambient, such as to increase reaction kinetics.

Recently, users of automated systems have noticed anomalous staining results under certain conditions, particularly during processing of samples using steps performed at temperatures above room temperature, and more particularly at temperatures near the boiling point of water or aqueous solutions. For example, such anomalous staining results have been more particularly noted during staining protocols that include processing steps performed at temperatures above 60° C., such as temperatures between about 90° C. and about 101° C. Certain such staining protocols result in well-defined, generally circular, areas of anomalously reduced staining intensity surrounded by areas of appropriately stained tissue. These areas of reduced staining intensity are referred to herein as spots. While spots are not known to have compromised sample examination, a preferred staining process nevertheless would address production of anomalously stained samples.

SUMMARY

The present invention provides reagents, compositions, and methods for their use, particularly in automated apparatuses, that reduce or substantially eliminate the occurrence of spots upon staining. Disclosed embodiments concern histochemical process compositions, exemplified herein by particular reference to cell conditioning compositions, comprising at least one nanoparticle in amounts effective to reduce the average number of spots per slide. Compositions comprising nanoparticles also may be referred to herein as nanosolutions.

One embodiment of an exemplary cell conditioning composition, referred to as CC1, comprises Tris borate-ethylene diamine tetraacetic acid (EDTA) buffer, at a pH of about 8, and from greater than zero to at least about 25 parts per million, more typically from about 2 parts per million to about 20 parts per million, and even more typically from about 2.5 parts per million to about 15 parts per million, of at least one nanoparticle. Another exemplary embodiment of a cell conditioning composition, referred to as CC2, comprises from about 5 mM to about 50 mM citrate buffer at a pH of from about 4 to about 8, about 1% to about 10% ethylene glycol, about 0.1 to about 10 mM sodium metabisulfite, about 0.1% to about 10% sodium dodecyl sulfate (SDS), and again from greater than zero to at least about 25 parts per million, more typically from about 2 parts per million to about 20 parts per million, and even more typically from about 2.5 parts per million to about 15 parts per million, of at least one nanoparticle.

The nanoparticle or nanoparticles used to form such compositions can be any of various nanoparticles, or combinations thereof, that reduce the average number of spots that may occur as a result of using a particular histochemical process reagent or composition. Classes of nanoparticles that can be used include metals, metalloids, functionalized metals or metalloids, metal alloys, metal oxides, ceramics, and other miscellaneous nanoparticles, such as carbon nanoparticles and diamond nanoparticles. Metal oxides, such as alumina ($Al_2O_3$), silica ($SiO_2$) and titania ($TiO_2$), have been used in working embodiments.

Embodiments of a method for using histochemical process nanosolutions also are disclosed. One embodiment concerns applying a histochemical process composition to a sample, the composition comprising at least one nanoparticle in an amount effective to reduce the average number of spots per slide relative to performing the process without using a nanosolution. A histochemical staining process is then performed on the sample. For example, the method may concern performing cell conditioning on the sample using a cell conditioning composition. The method also can include performing at least one or plural additional process steps typically practiced in a sample staining protocol. Additional staining processes, such as counter staining, also can be performed. Particular embodiments concern automated histochemical processes comprising dispensing a nanosolution onto a sample using an automated system, heating the sample, and performing a sample staining process on the sample.

The foregoing and other objects, features, and advantages of the invention will become more apparent from the following detailed description, which proceeds with reference to the accompanying figures.

DETAILED DESCRIPTION

I. Terms and Introduction

Figure 1:
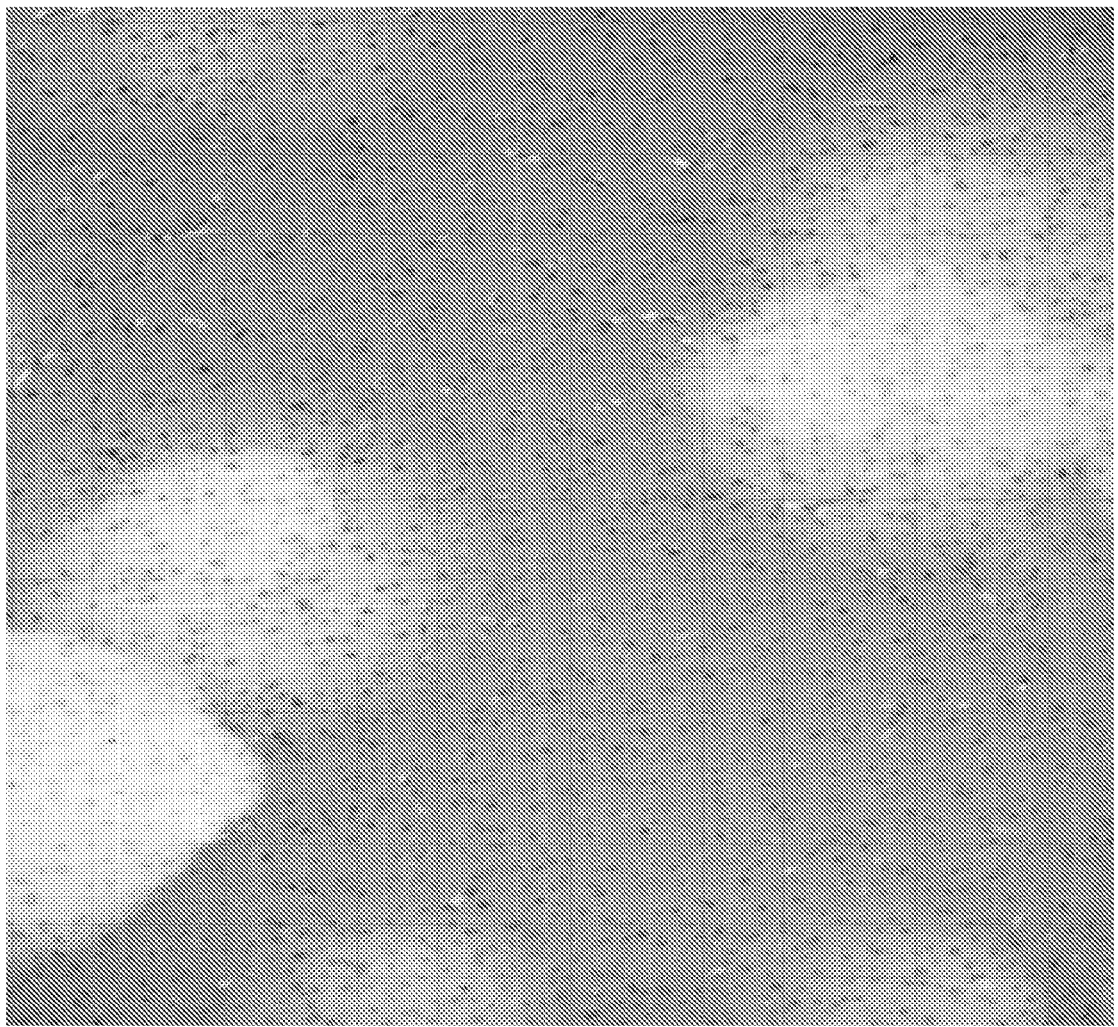
FIG. 1 is a photograph of stained bovine brain tissue illustrating the presence of spots.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that, unless stated otherwise, all numerical ranges, such as greater than 0 to at least 25 parts per million, include all integer and non-integer values between the stated numerical end points. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of specific terms are provided:

Additive, Buffer, Component, Cell Conditioner, Reagent, and Solution: Suitable compositions for practicing disclosed embodiments of the present invention, particularly cell conditioning compositions, may include, but are not limited to, the following reagent, reagents, or compositions thereof, where the reagents are available commercially, such as from Sigma Chemical, unless otherwise noted: 5 mM citrate at about pH 6; 5 mM citrate with about 0.5% sodium dodecyl sulfate (SDS) at about pH 6; 10 mM citrate at about pH 6; 10 mM citrate with about 0.5% SDS at about pH 6; 20 mM citrate at about pH 6; 20 mM citrate with about 0.5% SDS at about pH 6; 50 mM citrate at about pH 6; 50 mM citrate with about 0.5% SDS at about pH 6; 1 mM ethylene diamine tetraacetic acid (EDTA) at about pH 8; 1 mM EDTA with about 0.075% SDS at about pH 8; 10 mM EDTA at about pH 8; 10 mM EDTA with about 0.075% SDS at about pH 8; 20 mM EDTA at about pH 8; 20 mM EDTA with about 0.075% SDS at about pH 8; 50 mM EDTA at about pH 8; 50 mM EDTA with about 0.075% SDS at about pH 8; 10 mM citrate with about 0.5% SDS and about 1% ethylene glycol at about pH 6; 10 mM citrate with about 0.5% SDS and about 5% ethylene glycol at about pH 6; 10 mM citrate with about 0.5% SDS and about 10% ethylene glycol at about pH 6; 1 mM EDTA with about 0.075% SDS and about 1% ethylene glycol at about pH 8; 1 mM EDTA with about 0.075% SDS and about 5% ethylene glycol at about pH 8; 1 mM EDTA with about 0.075% SDS and about 10% ethylene glycol at about pH 8; phosphate/citrate/EDTA at about pH 9; 10 mM citrate with about 10 mM urea at about pH 6; 10 mM citrate with about 1 mM urea at about pH 6.2; 10 mM sodium citrate with about 1.4 mM $MgCl_2$ and about 0.1% SDS at about pH 7; 10 mM sodium citrate with about 1.4 mM $MgCl_2$ and about 0.1% SDS at about pH 7.99; 10 mM Tris-Cl at about pH 8; 10 mM Tris-Cl with about 20% formamide at about pH 8; 10 mM citrate with about 5% dimethyl sulfoxide (DMSO) at about pH 6; 10 mM citrate with about 0.1% Triton X-100 and about 20% formamide at about pH 6; 10 mM phosphate with 5×SSC and about 2.5% chrondroitin A at about pH 7; 10 mM Tris-Cl with about 10 mM EDTA and about 0.1% Triton X-100 and about 20% formamide at about pH 8.2; 10 mM citrate with about 20% glycerol at about pH 6; mM citrate with about 0.1% Triton X-100 and about 10 mM glycine at about pH 6; 1 mM EDTA with about 1 mM citrate and about 0.25% SDS at about pH 7.8; Norpar/mineral oil (high temperature coverslip); PAG-100 oil; 10 mM citrate with about 2% SDS at a pH of about 6 to about 6.2; 10 mM citrate with about 1% SDS at a pH of about 6 to about 6.2; 10 mM citrate with about 0.5% SDS at a pH of about 6 to about 6.2; 10 mM citrate with about 0.25% SDS at a pH of about 6 to about 6.2; 1 mM EDTA with about 2% SDS at a pH of about 7.5 to about 8; 1 mM EDTA with about 1% SDS at a pH of about 7.5 to about 8; 1 mM EDTA with about 0.5% SDS at a pH of about 7.5 to about 8; 1 mM EDTA with about 0.25% SDS at a pH of about 7.5 to about 8;

1 mM EDTA with about 0.1% SDS at a pH of about 7.5 to about 8; 1 mM EDTA with about 0.075% SDS at a pH of about 7.5 to about 8; 0.5 mM EDTA with about 0.25% SDS at about pH 8; 10 mM EDTA with about 0.5% SDS at about pH 9.6. A person of ordinary skill in the art will recognize that the concentrations stated above may be varied without altering the characteristics of the reagent, buffer, additive or solution for cell conditioning.

Certain disclosed cell conditioning compositions comprise 10 mM Tris base, 7.5 mM boric acid, 1 mM EDTA (disodium salt), 0.05% ProClin™300 (Supelco, Inc., Bellefonte, Pa.) at pH 8.5. Other embodiments contemplated include the basic formulation wherein the Tris base concentration ranges from about 5 mM to about 20 mM, wherein the boric acid concentration ranges from about 5 mM to about 40 mM, wherein the EDTA concentration ranges from about 0.5 mM to about 2 mM or wherein the pH ranges from about pH 7 to about pH 9.

Other embodiments contemplated include, but are not limited to: citrate buffer (a combination of sodium citrate trisodium salt dihydrate and citric acid hydrate); 10 mM Tris+20 mM boric acid+1 mM EDTA; 10 mM Tris+20 mM boric acid; 10 mM Tris+1 mM EDTA; 10 mM Tris; 20 mM boric acid; 1 mM EDTA; 20 mM Tris+20 mM boric acid+1 mM EDTA; 5 mM Tris+20 mM boric acid+1 mM EDTA; 10 mM Tris+20 mM boric acid+2 mM EDTA; 10 mM Tris+20 mM boric acid+0.5 mM EDTA; 10 mM Tris+40 mM boric acid+1 mM EDTA; 10 mM Tris+10 mM boric acid+1 mM EDTA; 10 mM Tris+5 mM boric acid+1 mM EDTA; 10 mM Tris+7.5 mM boric acid+1 mM EDTA; 10 mM Tris+20 mM boric acid+1 mM EDTA+5% ethylene glycol; 10 mM Tris+20 mM boric acid+5% ethylene glycol; 10 mM Tris+20 mM boric acid+1 mM EDTA+0.1% SDS; 10 mM Tris+20 mM boric acid+0.1% SDS; 10 mM Tris+20 mM boric acid+1 mM EDTA+5% DMSO; 10 mM Tris+20 mM boric acid+5% DMSO; 10 mM Tris+20 mM boric acid+1 mM EDTA-10% DMSO; 10 mM Tris+20 mM boric acid+10% DMSO; 10 mM Tris+20 mM boric acid+1 mM EDTA+5% formamide; 10 mM Tris+20 mM boric acid+5% formamide; 10 mM Tris+20 mM boric acid+1 mM EDTA+10% formamide; 10 mM Tris+20 mM boric acid+10% formamide; 10 mM Tris+20 mM boric acid+1 mM EDTA+0.5% Brij 35; 10 mM Tris+20 mM boric acid+0.5% Brij 35; 10 mM Tris+20 mM boric acid+1 mM EDTA+0.1% Brij 35; 10 mM Tris+20 mM boric acid+0.1% Brij 35; 10 mM Tris+20 mM boric acid+1 mM EDTA+0.5% Triton X-100; 10 mM Tris+20 mM boric acid+0.5% Triton X-100.

Additive, Component, Reagent and Solution: As used herein for exposing or deparaffinizing (i.e., the process of deparaffinization), such terms may include, but are not limited to, the following reagent, reagents, or compositions thereof, where the reagents are available commercially, such as from Sigma Chemical: de-ionized water, de-ionized water with about 0.1% Triton X-100, 10 mM phosphate at around pH 6.1, 10 mM phosphate with about 0.1% Triton X-100 at around pH 6.1, mM citrate at around pH 6, 10 mM citrate with about 0.1% Triton X-100, 2×SSC, 10 mM Tris[hydroxymethyl]aminomethane chloride (i.e., Tris-Cl) at around pH 8.2, 10 mM Tris-Cl with about 0.1% Triton X-100 at around pH 8.2. A person of ordinary skill in the art to which this invention pertains will recognize that the concentration or concentrations of the component or components listed above may be varied without altering the characteristics of the reagent, buffer, additive or solution for exposing or deparaffinizing.

Amplification: Detecting a target using plural visualization complexes, where the complexes can be the same or different.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: "Antibody" collectively refers to immunoglobulins or immunoglobulin-like molecules (including by way of example and without limitation, IgA, IgD, IgE, IgG and IgM, combinations thereof, and similar molecules produced during an immune response in any vertebrate, for example, in mammals such as humans, goats, rabbits and mice) and antibody fragments that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4 M^{-1}$ greater or at least $10^5 M^{-1}$ greater than a binding constant for other molecules in a biological sample).

More particularly, "antibody" refers to a polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

This includes intact immunoglobulins and the variants and portions of them well known in the art. Antibody fragments include proteolytic antibody fragments [such as $F(ab')_2$ fragments, Fab' fragments, Fab'-SH fragments and Fab fragments as are known in the art], recombinant antibody fragments (such as sFv fragments, dsFv fragments, bispecific sFv fragments, bispecific dsFv fragments, $F(ab)'_2$ fragments, single chain Fv proteins ("scFv"), disulfide stabilized Fv proteins ("dsFv"), diabodies, and triabodies (as are known in the art), and camelid antibodies (see, for example, U.S. Pat. Nos. 6,015,695; 6,005,079, 5,874,541; 5,840,526; 5,800,988; and 5,759,808). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, $3^{rd}$ Ed., W.H. Freeman & Co., New York, 1997.

Antigen: A compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens. In one example, an antigen is a *Bacillus* antigen, such as γPGA.

Automated or Automatic: Refers to a system and/or process at least partially, and potentially substantially completely, controlled by one or more computers.

Biological Sample: This term includes, but is not limited to, any collection of cells (either loose or in tissue) that can be mounted on a standard glass microscope slide including, without limitation, sections of organs, tumors sections, bodily fluids, smears, frozen sections, blood, cytology preps, microorganisms, tissue arrays and cell lines.

Blocking Solution: A solution useful for preventing non-specific binding of a labeled target to a nucleic acid on a microarray. In one embodiment, blocking solution comprises phosphate buffer of any total salt concentration; proteinaceous material (e.g., gamma globulins, casein, or any other protein suitable for blocking nonspecific binding); and non-ionic detergent. Particular examples of blocking solutions include (a) a solution comprising phosphate buffer of 10-200 mM total salt concentration, 0.5-6% goat gamma globulins, 5-15% hydrolyzed casein, and 0.005-1% nonionic detergent, and (b) a solution comprising 75 mM potassium phosphate, 25 mM sodium phosphate, 55 mM NaCl, 3% goat gamma globulins, 13.4% hydrolyzed casein, and 0.05% "blocking detergent" and is referred to as "CHIPPREP™2."

Blocking Detergent: A constituent of blocking solution, such as a nonionic detergent that comprises polyoxyethylene (23) lauryl ether, having a molecular formula of $C_{12}H_{25}(OCH_2CH_2)_nOH$, where n is about 23. Suitable products are obtained from Sigma-Aldrich, Inc., St. Louis, Mo., in 2000, Product No. 858366, sold under the trademark BRIJ®35.

Cell Conditioning: A process of improving accessibility of histochemical process reagents or compositions, both biological and chemical reagents or compositions, to a desired molecular target.

Cell Conditioning Reagent: An aqueous solution useful for conditioning cell samples prior to hybridization. Exemplary cell conditioning reagents include those disclosed herein and in U.S. Pat. No. 6,855,552, which is incorporated herein by reference.

Cell Conditioning Solution: An example of a cell conditioning reagent. Exemplary cell conditioning solutions include (A) a composition comprising sodium citrate, citric acid, "cell conditioning preservative," and nonionic detergent; (B) a composition comprising a cell conditioning solution comprising 0.4-8.2 mM sodium citrate, 1.8-10 mM citric acid, 0.1-1% cell conditioning preservative, and 0.05-5% cell conditioning detergent, and (C) a composition comprising cell conditioning solution comprising 8.2 mM sodium citrate, 1.8 mM citric acid, 0.05% cell conditioning preservative, and 0.1% RIBOCC™ cell conditioning detergent. Additional information concerning such solutions appears in Analytical Morphology, Gu, ed., Eaton Publishing Co. (1997) at pp. 1-40, which is incorporated herein by reference.

Cell Conditioning Preservative: A constituent of cell conditioning solution. Exemplary cell conditioning preservatives include a composition comprising 2.3% 5-chloro-2-methyl-4-isothiazolin-3-one, 0.7% 2-methyl-4-isothiazolin-3-one, 94-95% modified glycol, and 2-3% alkyl carboxylate, as obtained from Sigma-Aldrich, Inc., St. Louis, Mo., Catalog No. 48125, and sold under the trademark PROCLIN®300, a registered trademark of Rohm and Haas Company.

Cell Conditioning Detergent: Another constituent of cell conditioning solution. Exemplary cell conditioning detergents include a product obtained from Sigma-Aldrich, Inc., St. Louis, Mo., and sold under the trademark TWEEN®, such as TWEEN®20 (polyoxyethylenesorbitan monolaurate), a registered trademark of ICI Americas, Inc.

Detectable Label: A detectable compound or composition that is attached directly or indirectly to another molecule, such as an antibody or a protein, to facilitate detection of that molecule. Specific, non-limiting examples of labels include fluorescent tags, enzymes, and radioactive isotopes.

Epitope: An antigenic determinant. These are particular chemical groups or contiguous or non-contiguous peptide sequences on a molecule that are antigenic, that is, that elicit a specific immune response. An antibody binds a particular antigenic epitope.

First Primary Prehybridization Detergent: Refers to a constituent of a primary prehybridization solution. Exemplary first primary prehybridization detergents include a product comprising t-octylphenoxypolyethoxyethanol as obtained from Sigma-Aldrich, Inc., St. Louis, Mo., having Product No. 21123, and sold under the trademark TRITON®X-100, a registered trademark of Union Carbide Corp.

First Wash Detergent: Refers to a constituent of wash solution. Exemplary first wash detergents include nonionic detergents that comprise octylphenol ethylene oxide condensate, such as TRITON®X-100.

Hapten: A molecule, typically a small molecule that can combine specifically with an antibody, but typically is substantially incapable of being immunogenic except in combination with a carrier molecule.

Hybridization Solution: An aqueous solution useful for hybridizing a nucleic acid probe to a target nucleic acid. "Hybridization solution" includes "in situ hybridization solution" and "microarray hybridization solution."

Immune Response: A response of a cell of the immune system, such as a B-cell, T-cell, macrophage or polymorphonucleocyte, to a stimulus. An immune response can include any cell of the body involved in a host defense response, for example, an epithelial cell that secretes interferon or a cytokine An immune response includes, but is not limited to, an innate immune response or inflammation.

In situ Hybridization Detergent: A constituent of in situ hybridization solution. Exemplary embodiments of in situ hybridization detergents include (A) nonionic detergents that comprise polyoxyethylene(23) lauryl ether, having a molecular formula of $C_{12}H_{25}(OCH_2CH_2)nOH$, where n is about 23 as obtained from Sigma-Aldrich, Inc., St. Louis, Mo., Product No. 858366, sold under the trademark BRIJ®35.

In situ Hybridization Solution: An aqueous solution useful for hybridizing a probe to a target nucleic acid for in situ hybridization processes. Exemplary embodiments of in situ hybridization solutions include SSPE, dextran sulfate sodium salt, average molecular weight 10,000, formamide, and non-ionic detergents, such as an "in situ hybridization detergent." More particular embodiments of in situ hybridization solutions include (A) 1×-5×SSPE, 10-50% dextran sulfate sodium salt, average molecular weight 10,000, 50-80% formamide, and 0.01-1% in situ hybridization detergent, and (B) 2×SSPE, 20% dextran sulfate sodium salt, average molecular weight 10,000, 80% formamide, and 0.05% in situ hybridization detergent, referred to as "RIBOHYBE™." RIBOHYBE™ is disclosed in U.S. Pat. No. 6,656,685, which is incorporated herein by reference.

Isolated: An "isolated" microorganism (such as a virus, bacterium, fungus, or protozoan) has been substantially separated or purified away from microorganisms of different types, strains, or species. Microorganisms can be isolated by a variety of techniques, including serial dilution and culturing. An "isolated" biological component (such as a nucleic acid molecule, protein or organelle) has been substantially separated or purified away from other biological components in the cell of the organism in which the component naturally occurs, such as other chromosomal and extra-chromosomal DNA and RNA, proteins, and organelles.

Mammal: This term includes both human and non-human mammals. Similarly, the term "subject" includes both human and veterinary subjects.

Microarray Hybridization Solution: An aqueous solution useful for hybridizing a probe to a target nucleic acid on a microarray. Exemplary embodiments of microarray hybridization solutions include SSPE, dextran sulfate sodium salt, average molecular weight 10,000, and formamide. A particular embodiment of a microarray hybridization solution comprises 6×SSPE, 20% dextran sulfate sodium salt, average molecular weight 10,000, and 10% formamide, and is referred to as "CHIPHYBE™" as disclosed in U.S. Pat. No. 6,656,685, incorporated herein by reference.

Microarray Cleaning Solution: A solution useful for removing LIQUID COVERSLP™ (see, e.g., U.S. Pat. Nos. 5,225,325 and 5,418,138, each of which is incorporated herein by reference) from a microarray following the hybridization and washing steps of microarray hybridization methods, thereby reducing the background signal observed upon analysis of the microarray. Microarray cleaning solution comprises "microarray cleaning detergent" diluted in water, preferably deionized water. A particular embodiment of a microarray cleaning solution comprises 0.1-5% microarray cleaning detergent, even more typically 1% microarray cleaning detergent, and is referred to as "CHIPCLEAN™."

Microarray Cleaning Detergent: A constituent of microarray cleaning solution and refers to any detergent that effectively removes LIQUID COVERSLIP™, or compounds or compositions having similar function, from a microarray. Microarray cleaning detergents typically comprise biodegradable anionic and nonionic surfactants and no phosphate. An exemplary microarray cleaning detergent is a product manufactured by Procter & Gamble, Inc., Cincinnati, Ohio, 45202, as disclosed in U.S. Pat. Nos. 5,990,065 and 6,069,122 (both of which are incorporated herein by reference), and sold under the trademark DAWN™, a registered trademark of Procter & Gamble, Inc. LIQUID COVERSLIP™ refers to compositions comprising paraffin (Norpar 15) and Oil Red O.

Molecule of Interest or Target: A molecule for which the presence, location and/or concentration is to be determined. Examples of molecules of interest include proteins and nucleic acid sequences tagged with haptens.

Monoclonal Antibody: An antibody produced by a single clone of B-lymphocytes or by a cell into which the light and heavy chain genes of a single antibody have been transfected.

Multiplex, -ed, -ing: Detection of multiple targets in a sample substantially simultaneously, or sequentially, as desired, using plural different conjugates. Multiplexing can include identifying and/or quantifying nucleic acids generally, DNA, RNA, peptides, proteins, both individually and in any and all combinations. Multiplexing also can include detecting two or more of a gene, a messenger and a protein in a cell in its anatomic context.

Nanoparticle: A particle having at least one dimension, such as a diameter, of less than about 100 nanometers. Suitable nanoparticles can be used for various purposes, including visualization and controlling and/or modifying thermal properties, such as heat transfer, of a composition. For instance, nanoparticles can control and/or modify the thermal properties of a composition by modifying properties, e.g., surface tension, of fluids as they interact with a surface.

Nanosolution: A nanosolution is any solution useful for practicing a histochemical process having at least one nanoparticle, and potentially plural different nanoparticles, in an amount effective to reduce or eliminate anomalous staining results, such as spots. An effective amount may vary but for working embodiments typically is from greater than zero to at least about 25 parts per million.

Prehybridization Solution: A solution applied to tissue samples prior to the hybridization step in automated in situ hybridization processes. "Prehybridization solution" includes "primary prehybridization solution" and "secondary prehybridization solution.

Primary Prehybridization Solution: An aqueous solution useful for treating tissue samples prior to hybridization, including for fixing samples after deparaffinization. Exemplary embodiments include (A) an aqueous solution comprising sodium chloride, sodium phosphate dibasic, sodium phosphate monobasic, EDTA, "first primary prehybridization detergent," "second primary prehybridization detergent," and formalin; (B) a solution comprising 0.15-1.5 M sodium chloride, 8-80 mM sodium phosphate dibasic, 2-20 mM sodium phosphate monobasic, 1-10 mM EDTA, 0.0125-0.125% first primary prehybridization detergent, 0.00375-0.0375% second primary prehybridization detergent, and 10-40% formalin; and (C) 0.3 M sodium chloride, 16 mM sodium phosphate dibasic, 4 mM sodium phosphate monobasic, 2 mM EDTA, 0.025% first primary prehybridization detergent, 0.0075% second primary prehybridization detergent, and 30% formalin, referred to as "RIBOPREP™"

Polypeptide: A polymer comprising amino acid residues joined by amide bonds. "Polypeptide" and "protein" encompass any amino acid sequence and include modified sequences such as glycoproteins. The term "polypeptide" is specifically intended to cover naturally occurring proteins, as well as those which are recombinantly or synthetically produced.

Post-Hybridization Fixing Solution: A solution useful for fixing samples after hybridization for in situ hybridization processes. One embodiment of a post-hybridization fixing solution is RIBOFIX™, which is identical to RIBOPREP™.

Protein: A molecule, particularly a polypeptide, comprised of amino acids.

Residue: The term "residue" or "amino acid residue" includes reference to an amino acid that is incorporated into a protein, polypeptide, or peptide.

Sample: A biological specimen containing a biological molecule, such as DNA, RNA (including mRNA), protein, or combinations thereof, obtained from a subject. Examples include, but are not limited to, peripheral blood, urine, saliva, tissue biopsy, surgical specimen, amniocentesis samples and autopsy material.

Second Primary Prehybridization Detergent: A constituent of primary prehybridization solution. Exemplary second primary prehybridization detergents include (A) a nonionic detergent comprising polyoxyethylene (23) lauryl ether, having a molecular formula of $C_{12}H_{25}(OCH_2CH_2)_nOH$, where n is about 23, and (B) a product obtained from Sigma-Aldrich, Inc., St. Louis, Mo., Product No. 858366, sold under the trademark BRIJ® 35, a registered trademark of ICI Americas, Inc.

Secondary Prehybridization Solution: A hydrochloric acid solution suitable as a secondary pretreatment reagent in in situ hybridization protocols. Exemplary embodiments of secondary prehybridization solution comprise (A) 0.1-1 N HCl, and (B) a 0.3 N HCl composition referred to as RIBOCLEAR™.

Second Wash Detergent: A constituent of wash solution, such as BRIJ® 35.

Spreading Enhancer Solution (SES): A solution useful for reducing non-specific hybridization and facilitating initial slide surface coverage for automated microarray hybridization. Exemplary SESs comprise a buffer (e.g., SSPE) and a nonionic detergent. Particular SES embodiments include (A) a composition comprising 4×-8×SSPE and 8-12% "spreading enhancer detergent;" and (B) a composition comprising 6×SSPE and 10% spreading enhancer detergent, referred to as CHIPPREP™ 1.

Spreading Enhancer Detergent: A constituent of spreading enhancer solution, such as a detergent comprising polyoxyethylene (20) sorbitan monolaurate. A particular embodiment of a spreading enhancer detergent is a product obtained from Sigma-Aldrich, Inc., St. Louis, Mo., in 2000, Product No. 274348, sold under the trademark TWEEN®20.

SSC: A solution comprising sodium chloride and sodium citrate.

SSPE: Another constituent of in situ hybridization solution, and which is a common buffer used in many biochemical methods. SSPE comprises 3 M NaCl, 40 mM sodium phosphate monobasic, 160 mM sodium phosphate dibasic, and 20 mM EDTA.

Specific Binding Moiety: A member of a specific-binding pair. Specific binding pairs are pairs of molecules that are characterized in that they bind each other to the substantial exclusion of binding to other molecules. Particular examples of specific binding moieties include specific binding proteins (for example, antibodies, lectins, avidins such as streptavidins, and protein A), nucleic acids sequences, and protein-nucleic acids.

Specific Hybridization: Refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially identical to the target polynucleotide.

Stain: Any biological or chemical entity which, when applied to targeted molecules in biological sample, renders the molecules detectable under microscopic examination. Stains include, without limitation, detectable nucleic acid probes, antibodies, dyes and other reagents which in combination or by themselves result in a colored end product (by bright field or fluorescence detection methodologies).

Stringent Hybridization: Includes conditions that will typically include salt concentrations of less than about 1M, more usually less than about 500 mM, and preferably less than about 200 mM. Hybridization temperatures can be as low as 5° C., but are typically greater than 22° C., more typically greater than about 30° C., and preferably in excess of about 37° C.

Targeted Molecules: Detectable molecules found in cells including, without limitation, nucleic acids, proteins, carbohydrates, lipids, and small molecules.

Tissue: Any collection of cells that can be mounted on a standard glass microscope slide including, without limitation, sections of organs, tumors sections, bodily fluids, smears, frozen sections, cytology preps, and cell lines.

Treating or Treatment: Concerns applying a stain to a tissue as well as other processes associated with such application including, without limitation, heating, cooling, washing, rinsing, drying, evaporation inhibition, deparaffinization, cell conditioning, mixing, incubating, evaporation, and any and all combinations of such processes.

Wash Solution: An aqueous solution useful for washing samples after the hybridization step for in situ hybridization and microarray hybridization processes. Wash solution is useful for washing samples either when an RNA probe (riboprobe) or a DNA probe (oligoprobe) is used. Exemplary embodiments of wash solution include (A) a composition comprising sodium chloride, phosphate buffer, EDTA, and one or more nonionic detergents, (B) a composition comprising two nonionic detergents, a "first wash detergent" and "second wash detergent;" (C) a composition comprising 0.1-0.5 M sodium chloride, 5-30 mM sodium phosphate dibasic, 1-10 mM sodium phosphate monobasic, 0.5-5 mM EDTA, 0.01-0.1% first wash detergent, and 0.0025-0.025% second wash detergent; and (D) a composition comprising 0.3 M sodium chloride, 16 mM sodium phosphate dibasic, 4 mM sodium phosphate monobasic, 2 mM EDTA, 0.025% first wash detergent, and 0.0075% second wash detergent, referred to as RIBOWASH™.

10×SSC: A 10 molar concentration of sodium chloride/sodium citrate solution, comprising deionized water as needed to make a liter solution, 87.66 grams NaCl, 44.12 grams citric acid trisodium salt, adjusted to pH 7.0 with HCl or NaOH, as appropriate. 0.5 ml ProClin 300 is added as preservative.

II. Automated Histochemical Sample Treatment

The assignee of the present technology, Ventana Medical Systems, Inc., is a world leading authority in compositions and methods for performing histochemical analyses, as well as automated apparatuses therefore, including the commercially available Benchmark, Benchmark XT, Discovery, Discovery XT and Sympony apparatuses. Various aspects of automated molecular pathology apparatuses, methods for their use and compositions used for such methods, are described in U.S. Pat. Nos. 6,045,759, 6,296,809, 6,544,798, 6,582,962, 6,855,552, 6,855,559, 6,933,117, 7,067,325, 7,270,785, each of which is incorporated herein by reference. A brief discussion of such apparatuses and methods for their use is provided below.

Automated apparatuses are designed to automatically stain or otherwise treat tissue mounted on microscope slides with an appropriate reagent, reagents, or compositions thereof, in a desired sequence, for a particular time and at a temperature effective to provide the desired result. Stained tissue sections are then viewed under a microscope by a medical practitioner. Automated apparatuses also typically include other components, such as a host computer, a monitor, an input device, such as a keyboard and mouse, bulk fluid containers, at least one waste container and related equipment. Additional staining modules or other instruments may be added to form a network.

One exemplary configuration of an auatomated apparatus is generally described in U.S. Pat. No. 6,045,759, as well as in the Ventana NexES User's Guide available from Ventana Medical Systems, Inc. (Tucson, Ariz.), which also is incorporated herein by reference. The apparatus is a microprocessor-controlled staining instrument. A slide carousel supporting radially positioned glass slides is revolved by a stepper motor to place each slide under one of a series of reagent dispensers. The apparatus controls reagent dispensing, washing, mixing, and heating. The slide carousel may include a plurality of thermal platforms that are mounted radially about the perimeter of a carousel upon which standard glass slides with tissue samples may be placed. A circuit board is also mounted to the slide carousel to monitor the sensors and to control the heaters. For certain disclosed embodiments the slide heating system rapidly heats the useful area of the slide to about 95° C. in under two minutes. A processor controls the temperature of the slides by modifying the heat to the slides in order for the slides' temperature to be at the target temperature. If the temperature of the slide is less than the target temperature, a slide heater is activated. If the temperature of the slide is greater than the target temperature, a cooler is activated.

A reagent carousel includes reagent dispensers for dispensing reagents onto slides. Reagents may include any chemical or biological material conventionally applied to slides including nucleic acid probes or primers, polymerase, primary and secondary antibodies, digestion enzymes, pre-fixatives, post-fixatives, readout chemistry, and counterstains. For each slide processed by the apparatus, a reagent or reagents is applied and then incubated for a precise time period in a temperature-controlled environment. After the appropriate incubation period, the reagent is washed off the slide using wash dispense nozzles. Remaining wash buffer volume is adjusted using a volume adjust nozzle. Coverslip™ solution is applied to inhibit evaporation using a dispense nozzle. These steps are repeated as the carousel rotates until a desired protocol is completed.

Automated histochemical apparatuses may be used to perform in situ hybridization (ISH), in situ PCR, immunohistochemistry (IHC), other chemical (non-biological) tissue staining techniques, etc. Many of the process steps must be carefully temperature controlled for a precise period of time. Different specimens may require different temperatures depending on the process being used, how the tissue was prepared and fixed, etc. For example, heating the tissue in an appropriate aqueous solution improves the accessibility of the target molecule to the stain (e.g., protein, nucleic acid, carbohydrate, lipid, or small molecule). For example, citrate buffer is a suitable conditioning solution for: DNA, at a temperature of up to about 95° C.; for protein targets at a temperature up to about 100° C., for about 42 minutes; and for RNA targets at a temperature up to about 75° C. for about one hour. Many alternative cell conditioning reagents or compositions, in addition to citrate buffer, may be used, including those described specifically herein as well as the definition section.

III. Process Solutions Comprising Nanoparticles

Figure 2:
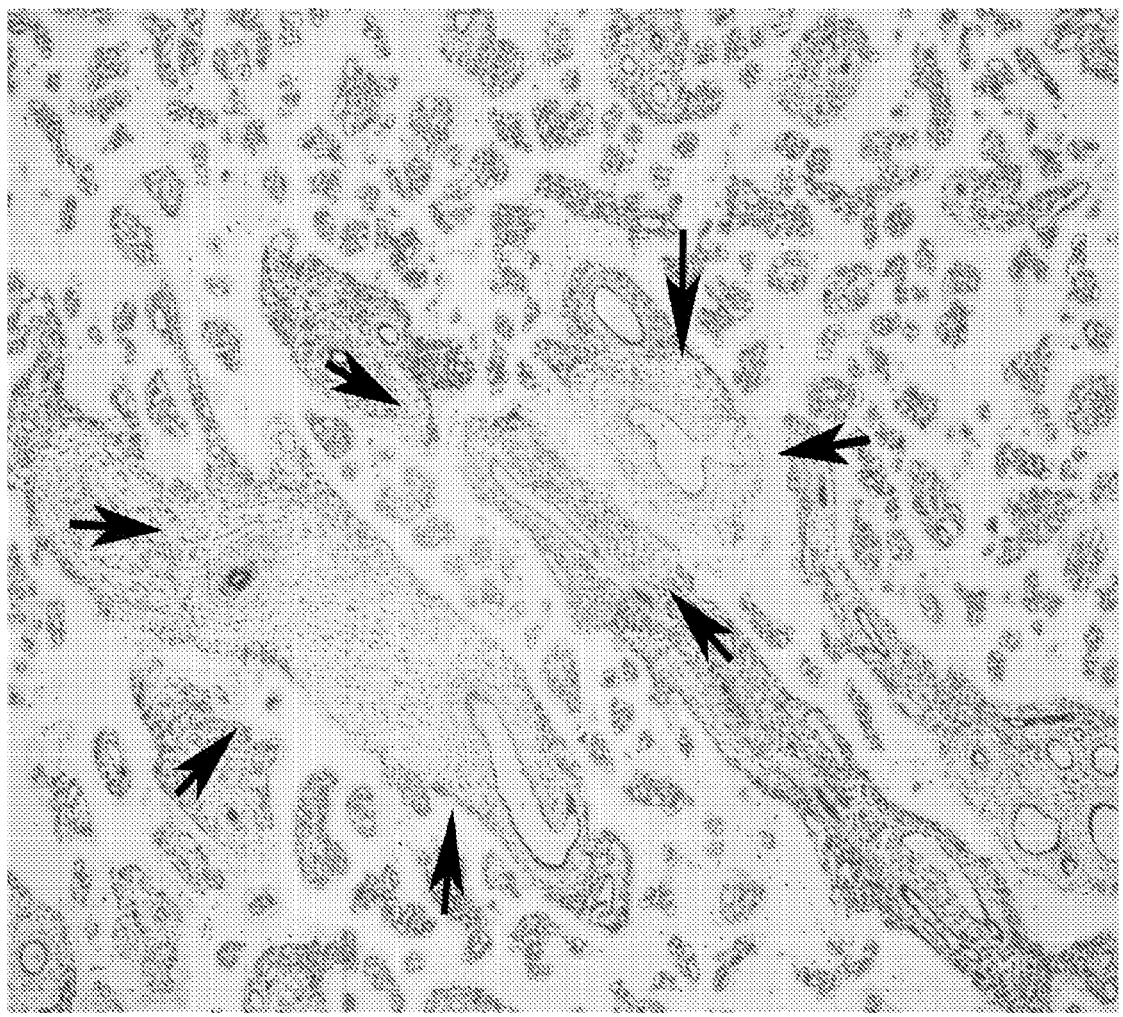
FIG. 2 is a photograph of stained human placenta illustrating the presence of spots.

Recently, anomalous staining results, particularly spots, were observed when certain histochemical process steps were performed using automated histochemical process apparatuses, as exemplified by cell conditioning at a temperature greater than ambient, without using solutions comprising nanoparticles. See, for example, FIG. 1, which is a photograph of stained bovine brain tissue illustrating the presence of spots. FIG. 2 also illustrates the production of spots when human placenta is stained. Accordingly, disclosed embodiments of the present invention concern histochemical nanosolutions, and embodiments of a method for making and using such histochemical nanosolutions to address the production of undesired spotting. For example, disclosed embodiments concern any process solution used during a staining process, in situ hybridization (ISH), in situ PCR, immunohistochemistry (IHC), etc., as well as a variety of chemical (non-biological) tissue staining techniques, to which a nanoparticle, or nanoparticles, is added to reduce or eliminate spots. Histochemical nanosolutions are even more particularly used in process steps, particularly automated processes, that are practiced at temperatures greater than ambient, and more typically at temperature of from about 60° C. to about 101° C. Reagents or compositions used for histochemical processes can be aqueous or organic suspensions or solutions, but most typically are aqueous solutions of a single reagent or multiple reagents.

Figure 3:
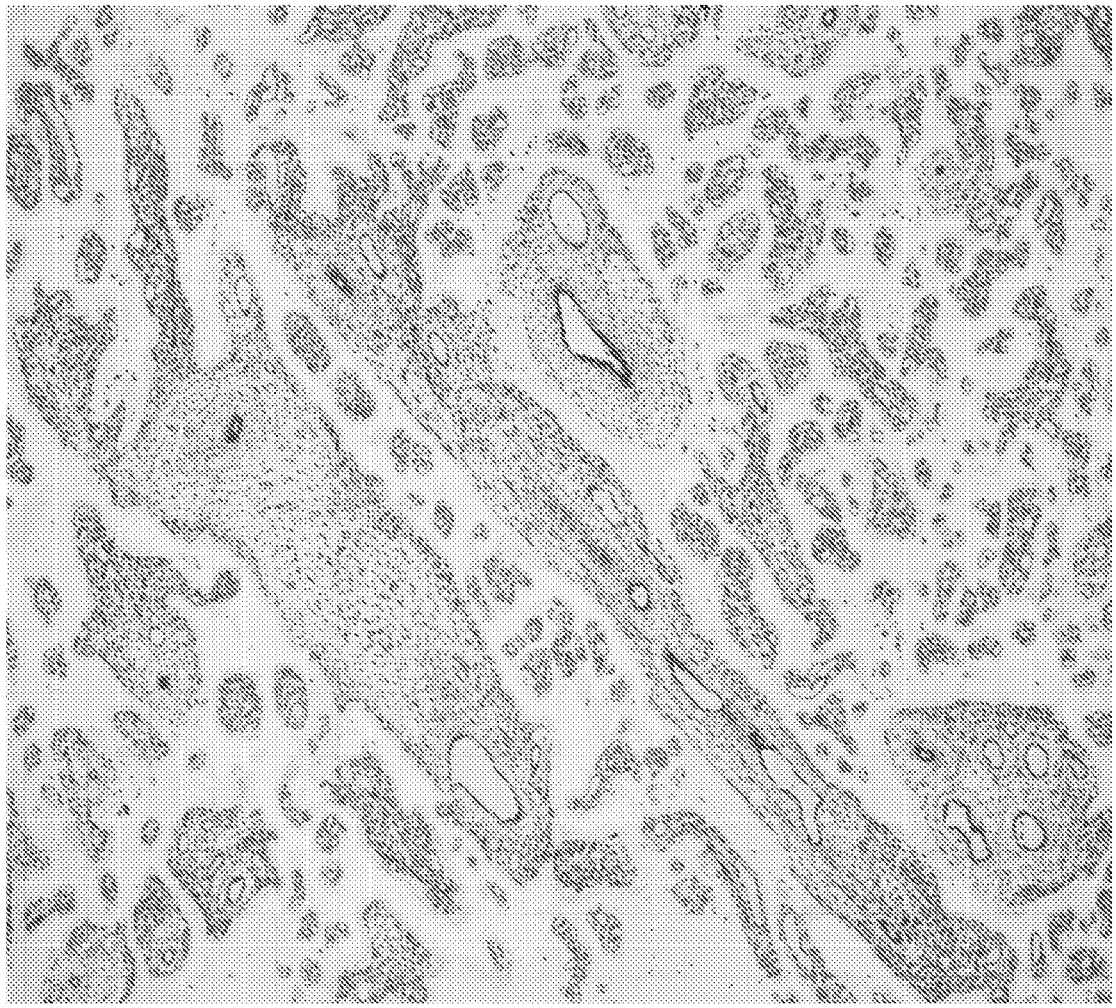
FIG. 3 is a photograph of human placenta prepared according to disclosed embodiments of the present invention illustrating a reduction in the occurrence of spots.

Adding nanoparticles to a fluid substantially improves the fluid's capability to transfer heat. See, for example, I. C. Bang et al., "Boiling Heat Transfer Performance and Phenomena of $Al_2O_3$-Water Nano-fluids from a Plain Surface in a Pool," *Int. J. Heat Mass Transfer* 48, pp. 2407-2419 (2005). Using histochemical process solutions that include nanoparticles substantially eliminates the occurrence of spots. See FIG. 3. Thus, in general, any reagent, reagents or compositions thereof that are applied to a sample as a solution, followed by a heating step, can be formulated as a nanosolution for practicing disclosed embodiments of the present invention. For example, nanoparticles can be added to various additives, buffers, reagents, cell conditioners, etc. to enhance the ability of such materials for use in histochemical analyses. Exemplary process solutions, and exemplary suitable nanoparticles useful for making histochemical nanosolutions, are discussed in more detail below.

A. Cell Conditioning Compositions

With reference to cell conditioning reagents and compositions to illustrate the invention, for DNA targets a cell conditioning solution may be a nanosolution of EDTA comprising from greater than 0 to about 25 ppm of a suitable nanoparticle. Such solutions are typically used at a common temperature setting of about 95° C. for an effective period of time, such as from about 2 to about 90 minutes.

The reagents used for cell conditioning can be the same as those for exposing the embedded biological sample. For example, for DNA targets, another example of a cell conditioning solution may be a nanosolution of SSC comprising from greater than 0 to about 25 ppm of a suitable nanoparticle. Such compositions typically are used at a common temperature of about 95° C. for a duration ranging from about 2 to about 90 minutes. As yet another option, for DNA targets the cell conditioning solution may be a nanosolution of sodium citrate comprising from greater than 0 to about 25 ppm of a suitable nanoparticle. Such compositions typically are used at a common temperature of about 90° C. for a duration ranging from about 2 to about 90 minutes.

For RNA targets, a suitable cell conditioning solution may be a nanosolution of SSC comprising from greater than 0 to about 25 ppm of a suitable nanoparticle. Such solutions typically are used at a common temperature of about 75° C. for an effective period of time of from about 2 to about 90 minutes.

For protein targets, a suitable cell conditioning solution is a nanosolution of boric acid buffer comprising from greater than 0 to about 25 ppm of a suitable nanoparticle. Such solutions typically are used at a common temperature setting of greater than about 100° C. for an effective period of time, such as from about 2 to about 90 minutes. Another example of a cell conditioning solution for protein targets is a nanosolution of phosphate buffer comprising from greater than 0 to about 25 ppm of a suitable nanoparticle. Such compositions typically are used at a common temperature setting in excess of 100° C. for an effective period of time such as from about 2 to about 90 minutes. As yet another option for protein targets, a cell conditioning solution may be a nanosolution of urea comprising from greater than 0 to about 25 ppm of a suitable nanoparticle. Such compositions typically are used at a common temperature setting of greater than 100° C. for an effective period ranging from about 2 to about 90 minutes.

For histochemical reactions, such as a Hematoxylin and Eosin (H&E) stain, a cell conditioning nanosolution may be treated de-ionized water comprising from greater than 0 to about 25 ppm of a suitable nanoparticle. Such solutions typically are used at a temperature of from about 60° C. to about 80° C. for an effective period of time of from about 2 to about 90 minutes. Sodium dodecyl sulfate (SDS) and/or ethylene glycol also may be added to the conditioning solution.

For histochemical reactions, such as a Trichrome stain, a cell conditioning nanosolution may be Bouins fixative [750 ml picric acid, saturated aqueous solution, 250 ml 37-40% formalin (formaldehyde), 50 ml glacial acetic acid] comprising from greater than 0 to about 25 ppm of a suitable nanoparticle. Such compositions are used at a temperature of from about 60° C. to about 80° C. for an effective period of time of from about 2 to about 30 minutes. As another option for histochemical reactions, such as an Acid Fast Bacilli (AFB) stain, a cell conditioning nanosolution may be peanut oil comprising from greater than 0 to about 25 ppm of a suitable nanoparticle and a common temperature range is from about 60° C. to about 70° C.

For whole cells, a cell conditioning solution may be a nanosolution of a lower (10 carbon atoms or fewer) alkyl alcohol, such as methanol. Such compositions are used at ambient conditions for an effective period ranging from about 4 to about 10 minutes.

For all aqueous-based compositions disclosed herein, such compositions also can include, either as a replacement for water, or as an additive in addition to water, an alcohol, glycol or polyglycol. For example, such solutions can include ethylene glycol as a replacement for or in addition to the water used to formulate such compositions.

B. Exemplary Working Embodiments of Process Compositions Used with Automated Histochemical Apparatuses One disclosed embodiment of a cell conditioner (cell conditioning solution 1 or CC1) used by the assignee of the present invention for its automated histochemical apparatuses is a composition comprising Tris borate-ethylene diamine tetraacetic acid (EDTA) buffer, at a pH of about 8. CC1 can be formulated as a nanosolution by adding an effective amount, e.g. greater than 0 to at least about 25 parts per million, of at least one nanoparticle to the composition.

A second disclosed embodiment of a cell conditioner (cell conditioning solution 2 or CC2) comprises about 10 mM citrate buffer at about pH 6, about 5% ethylene glycol, about 1 mM sodium metabisulfite (Morphosave™, Ventana Medical Systems, Inc., Tucson, Ariz.; U.S. Pat. No. 5,432,056) and about 0.3% sodium dodecyl sulfate (SDS). The concentration of citrate may range from about 5 mM to about 50 mM. The pH of the buffer may range from about 4 to about 8. The concentration of ethylene glycol may range from about 1% to about 10%. The concentration of sodium metabisulfite may range from about 0.1 mM to about 10 mM, preferably from about 0.5 mM to about 1.5 mM. The concentration of SDS may range from about 0.1% to about 1%, preferably from about 0.25% to about 0.5%. CC2 can be formulated as a nanosolution by adding an effective amount, e.g. greater than 0 to at least about 25 parts per million, of at least one nanoparticle to the composition.

Additional exemplary histochemical nanosolutions are provided below.

TABLE 1

EZ Prep Nanosolution

| Component | Amount |
| --- | --- |
| Deionized Water | as required to 1 L |
| Triton ® X-100 (Sigma) | 10 ml |

TABLE 1-continued

EZ Prep Nanosolution

| Component | Amount |
| --- | --- |
| ProClin ® 300 (Sigma) | 0.5 ml |
| Nanoparticle | 0-25 parts per million |

Triton ® X-100 is polyethylene glycol tert-octylphenyl ether, having a molecular formula of t-Oct-C$_6$H$_4$—(OCH$_2$CH$_2$)$_x$OH, x = 9-10.
ProClin ® 300 is a composition available from Sigma-Aldrich comprising 2.3% 5-chloro-2-methyl-4-isothiazolin-3-one, 0.70% 2-methyl-4-isothiazolin-3-one, 2-3% of an alkyl carboxylate and a 93-95% of a modified glycol.

TABLE 2

CC Plus Nanosolution

| Component | Amount |
| --- | --- |
| Deionized Water | 1000 ml |
| Tris Base (VWR) | 1.211 g (10 mM) |
| Boric Acid (Sigma) | 0.372 g (6 mM) |
| EDTA Disodium Salt Dihydrate (Sigma) | 0.46 g (1.25 mM EDTA) |
| ProClin ® 300 (Sigma) | 0.50 ml (0.05%) |
| Nanoparticle | 0-25 parts per million |

TABLE 3

RiboCC Nanosolution

| Component | Amount |
| --- | --- |
| Deionized Water | 1000 ml |
| Sodium Citrate dihydrate (Sigma) | 2.41 g (8.2 mM) |
| Citric Acid monohydrate (Sigma) | 0.38 g (1.8 mM) |
| Tween ® 20 (Sigma) | 1 ml (0.1%) |
| ProClin ® 300 (Sigma) | 0.50 ml (0.05%) |
| Nanoparticle | 0-25 parts per million |

Tween ® 20 is polyoxyethylenesorbitan monolaurate.

TABLE 4

RiboCC Plus Nanosolution

| Component | Amount |
| --- | --- |
| Deionized Water | 1000 ml |
| Sodium Citrate dihydrate (Sigma) | 2.41 g (8.2 mM) |
| Citric Acid monohydrate (Sigma) | 0.38 g (1.8 mM) |
| ProClin ® 300 (Sigma) | 0.50 ml (0.05%) |
| Nanoparticle | 0-25 parts per million |

C. Nanoparticles

A person of ordinary skill in the art will appreciate that nanoparticles suitable for forming histochemical process nanosolutions according to disclosed embodiments of the present invention can be any of various nanoparticles, or combinations thereof, such as nanoparticle(s) that reduce anomalous staining, particularly nanoparticles that reduce the average number of spots that may occur as a result of using a particular histochemical process composition. Several factors can be considered for selecting an appropriate nanoparticle or nanoparticles for use in histochemical analyses as disclosed herein, including compatibility with biological samples, toxicity to users, availability, cost, etc.

Solely by way of example and without limitation, a partial list of suitable nanoparticles includes: metals and metal alloys, including aluminum, copper, copper-zinc alloy, gold, gold colloid solution, Hastelloy® C276 (a nickel-molybdenum-chromium alloy with added tungsten comprising approximately 55% Ni, 15-17% Mo, 14.5-16.5% Cr, 4-7% Fe and 3-4.5%), iron, iron-nickel alloy, molybdenum, nickel, palladium, platinum, silicon, silver, silver dispersion, silver-copper alloy, silver-platinum alloy, silver-tin alloy, tantalum, tin, titanium, tungsten, and zinc; metal oxides, including aluminum cerium oxide, aluminum oxide, antimony tin oxide, antimony (III) oxide, barium strontium titanium oxide, barium zirconate, bismuth cobalt zinc oxide, bismuth (III) oxide, calcium oxide, cerium (IV) oxide, cerium (IV)-zirconium (IV) oxide, chromium (III) oxide, cobalt aluminum oxide, cobalt (II, III) oxide, copper aluminum oxide, copper iron oxide, copper zinc iron oxide, copper (I) oxide, copper (II) oxide, dysprosium (III) oxide, erbium (III) oxide, europium (III) oxide, gadolinium (III) oxide, holmium (III) oxide, indium tin oxide, indium (III) hydroxide, indium (III) oxide, iron nickel oxide, iron (II, III) oxide, iron (III) oxide, lanthanum (III) oxide, magnesium hydroxide, magnesium oxide, magnetic iron oxide, neodymium (III) oxide, nickel chromium oxide, nickel cobalt, oxide, nickel zinc, iron oxide, nickel (II) oxide, praseodymium (III, IV) oxide, samarium strontium cobalt oxide, samarium (III) oxide, silica, silicon dioxide, alumina doped, terbium (III, IV) oxide, tin (IV) oxide, titanium silicon oxide, titanium (IV) oxide, titanium (IV) oxide, anatase, titanium (IV) oxide, mixture of rutile and anatase, titanium (IV) oxide, rutile, tungsten (VI) oxide, ytterbium (III) oxide, yttrium aluminum oxide, yttrium iron oxide, yttrium (III) oxide, zinc iron oxide, zinc oxide, zirconium (IV) oxide, and zirconium (IV) oxide-yttria stabilized; other ceramics, including aluminum nitride, aluminum titanate, barium ferrite, barium titanate (IV), amorphous calcium phosphate, calcium titanate, calcium zirconate, hydroxyapatite, magnesium aluminate, silicon carbide, silicon nitride, strontium ferrite, strontium titanate, titanium carbonitride, titanium carbonitride (7:3), titanium (IV) carbide, zinc titanate, and zirconium (IV) silicate; functionalized metals and metalloids, including (1-mercaptoundec-11-yl)tetra(ethylene glycol) functionalized gold nanoparticles solution, 1-mercapto-(triethylene glycol) methyl ether functionalized gold nanoparticles solution, 3-aminopropyl functionalized silica, 3-aminopropyl-(3-oxobutanoic acid) functionalized silica, decanethiol functionalized silver nanoparticles solution, dodecanethiol functionalized gold nanoparticles solution, dodecanethiol functionalized silver nanoparticles solution, and octanethiol functionalized gold nanoparticles solution; carbon and diamond; and any and all combinations thereof.

Particularly suitable nanonparticles are metal oxide nanoparticles, such as alumina ($Al_2O_3$), silica (SiO2), titania ($TiO_2$), and combinations thereof. Currently preferred nanoparticles, based on availability, cost and spot reduction, are silica nanoparticles.

Nanoparticles are added to various compositions useful for performing histochemical analyses, such as cell conditioning compositions, at suitable concentrations for performing such analyses. For disclosed embodiments, a nanoparticle, or combinations of nanoparticles, can be added to such compositions at a concentration of greater than zero to at least about 25 ppm, more typically from about 2 ppm to about 20 ppm, and even more typically from about 2.5 ppm to about 15 ppm. A person of ordinary skill in the art will appreciate that these concentrations can vary from that stated as long as such concentrations (1) do not preclude or interfere with successfully performing the desired molecular pathological analysis, and (2) desirably reduce or substantially eliminate the average number of staining spots that occur relative to compositions that do not include the nanoparticle or nanoparticles.

IV. Example

The following example is provided to illustrate particular features of certain working embodiments. A person of ordinary skill in the art will appreciate that the scope of the invention is not limited to the particular features disclosed by this example.

Example 1

Tissue slides of cow brain (30 slides) were prepared. In general, tissue samples were fixed in formalin, embedded in paraffin, gross cut into approximately one inch cubes, sliced into 8 μm sections, and placed onto glass slides. A Benchmark, or Benchmark XT, instrument was used to further process the slides. The slide-mounted tissue samples were deparaffinized using EZ Prep solution, followed by cell conditioning with a cell conditioning solution as indicated in below in Table 5. Histochemical analysis was then performed. For each of various reagent compositions tested, a first group of slides was prepared using a cell conditioning composition, such as CC1, but without the addition of nanoparticles to establish a control for the average number of spots per slide, and the standard deviation thereof. Thereafter, various nanosolutions, as indicated below in Table 5, were used to perform the histochemical analyses. The results of these tests are summarized below in Table 5.

TABLE 5

SPOT TEST RESULTS

| Composition | Average Total Spots | Standard Deviation of Total Spots |
|---|---|---|
| 1. CC1 (lot 540818) | 12.7 | 6.4 |
| 2. CC1 (lot 540818) + 2.5 mg/L $TiO_2$ | 9.6 | 5.1 |
| 3. CC1 (lot 540818) + 2.5 mg/L $Al_2O_3$ | 3.0 | 1.7 |
| 4. CC1 (lot 537661) | 13.1 | 4.7 |
| 5. CC1 (lot 537661) + 15 mg/L $Al_2O_3$ | 1.3 | 1.3 |
| 6. CC1 and new tissue block[1] | 8.4 | 4.0 |
| 7. CC1 and new tissue block + 5 mg/L $Al_2O_3$ | 0.6 | 0.5 |
| 8. CC1 and new tissue block + 10 mg/L $Al_2O_3$ | 1.2 | 0.8 |
| 9. CC1 and new tissue block + 5 mg/L $TiO_2$ | 4.2 | 2.7 |
| 9. CC1 and new tissue block + 10 mg/L $TiO_2$ | 3.0 | 2.3 |
| 10. CC1 and new tissue block + 2.5 mg/L $SiO_2$ | 3.0 | 1.8 |

TABLE 5-continued

SPOT TEST RESULTS

| Composition | Average Total Spots | Standard Deviation of Total Spots |
|---|---|---|
| 11. CC1 and new tissue block + 5 mg/L SiO$_2$ | 2.7 | 2.4 |
| 12. CC1 and new tissue block + 10 mg/L SiO$_2$ | 2.1 | 2.1 |
| 13. CC1 and new tissue block + 15 mg/L SiO$_2$ | 1.8 | 2.0 |
| 14. CC1 and new tissue block + 15 mg/L TiO$_2$ | 2.0 | 2.1 |
| 15. 10 mg/L SiO$_2$ with antibody at 1:400 | 1.1 | 1.1 |
| 16. Baseline antibody[2] at 1:400 | 2.0 | 1.6 |
| 17. Baseline antibody at 1:100 | NA | NA |
| 18. Baseline antibody at 1:400 | 0.9 | 1.0 |
| 19. Baseline antibody at 1:100 | 2.6 | 2.3 |
| 20. Baseline antibody at 1:100 | NA | NA |
| 21. Baseline antibody at 1:100 | 3.2 | 3.1 |
| 22. CC1 + antibody at 1:100 | 1.3 | 1.9 |
| 23. CC1 + antibody at 1:400 | 0.3 | 0.7 |
| 22. CC Plus + antibody at 1:100 + 10 ppm TiO$_2$ | 0.8 | 1.0 |
| 23. CC Plus + antibody at 1:400 + 10 ppm TiO$_2$ | 0.0 | 0.0 |

[1]"New tissue block": For the test results reported, hundreds of slides were required to replicate (from about 15 to about 30 trials/condition) different conditions tested. This required using different, i.e. new, tissue blocks.
[2]"Baseline antibody": Only one antibody (ubiquitin) was used. The antibody was used at two dilutions, 1:100 and 1:400, with 1:400 the likely dilution used for commercial embodiments. The 1:100 dilutions was used as a "worst case scenario" to deliberately over-stain, making spots easier to identify. "Baseline antibody" refers to the "new tissue block". Each new tissue block was stained with each of the two dilutions of antibody, using the standard staining conditions. After that, each new condition was compared to that baseline run for the tissue block.

The data provided by Table 5 clearly establishes that using nanosolutions for histochemical analyses substantially decreases the average number of spots per slide.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A histochemical process composition, comprising deionized water, Tris base, boric acid, EDTA disodium dehydrate, a composition comprising 5-chloro-2-methyl-4-isothiazolin-3-one 2.30%, 2-methyl-4-isothiazolin-3-one 0.70%, modified glycol 93-95%, alkyl carboxylate 2-3%, and greater than 0 to about 25 parts per million of at least one nanoparticle.

2. A histochemical process composition, comprising deionized water, sodium citrate dihydrate, citric acid monohydrate, polyoxyethylenesorbitan monolaurate, a composition comprising 5-chloro-2-methyl-4-isothiazolin-3-one 2.30%, 2-methyl-4-isothiazolin-3-one 0.70%, modified glycol 93-95%, alkyl carboxylate 2-3%, and greater than 0 to about 25 parts per million of at least one nanoparticle.

3. A histochemical process composition, comprising deionized water, sodium citrate dihydrate, citric acid monohydrate, 5-chloro-2-methyl-4-isothiazolin-3-one 2.30%, 2-methyl-4-isothiazolin-3-one 0.70%, modified glycol 93-95%, alkyl carboxylate 2-3%, and greater than 0 to about 25 parts per million of at least one nanoparticle.

4. The composition according to claim 1 where the nanoparticle is a metal or metal alloy.

5. The composition according to claim 4 where the nanoparticle is aluminum, copper, copper-zinc alloy, gold, gold colloid solution, a nickel-molybdenum-chromium alloy comprising approximately 55% Ni, 15-17% Mo, 14.5-16.5% Cr, 4-7% Fe and 3-4.5%, iron, iron-nickel alloy, molybdenum, nickel, palladium, platinum, silicon, silver, silver dispersion, silver-copper alloy, silver-platinum alloy, silver-tin alloy, tantalum, tin, titanium, tungsten, zinc, or combinations thereof.

6. The composition according to claim 1 where the nanoparticle is a metal oxide.

7. The composition according to claim 6 where the nanoparticle is aluminum cerium oxide, aluminum oxide, antimony tin oxide, antimony (III) oxide, barium strontium titanium oxide, barium zirconate, bismuth cobalt zinc oxide, bismuth (III) oxide, calcium oxide, cerium (IV) oxide, cerium (IV)-zirconium (IV) oxide, chromium (III) oxide, cobalt aluminum oxide, cobalt (II, III) oxide, copper aluminum oxide, copper iron oxide, copper zinc iron oxide, copper (I) oxide, copper (II) oxide, dysprosium (III) oxide, erbium (III) oxide, europium (III) oxide, gadolinium (III) oxide, holmium (III) oxide, indium tin oxide, indium (III) hydroxide, indium (III) oxide, iron nickel oxide, iron (II, III) oxide, iron (III) oxide, lanthanum (III) oxide, magnesium hydroxide, magnesium oxide, magnetic Iron oxide, neodymium (III) oxide, nickel chromium oxide, nickel cobalt, oxide, nickel zinc, iron oxide, nickel (II) oxide, praseodymium (III, IV) oxide, samarium strontium cobalt oxide, samarium(III) oxide, silica, silicon dioxide, alumina doped, terbium (III, IV) oxide, tin (IV) oxide, titanium silicon oxide, titanium (IV) oxide, titanium (IV) oxide, anatase, titanium (IV) oxide, mixture of rutile and anatase, titanium (IV) oxide, rutile, tungsten (VI) oxide, ytterbium (III) oxide, yttrium aluminum oxide, yttrium iron oxide, yttrium (III) oxide, zinc iron oxide, zinc oxide, zirconium (IV) oxide, zirconium(IV) oxide-yttria stabilized, or combinations thereof.

8. The composition according to claim 6 where the nanoparticle is alumina (Al$_2$O$_3$), silica (SiO$_2$), titania (TiO$_2$), or combinations thereof.

9. The composition according to claim 1 where the nanoparticle is a ceramic.

10. The composition according to claim 9 where the nanoparticle is aluminum nitride, aluminum titanate, barium ferrite, barium titanate (IV), amorphous calcium phosphate, calcium titanate, calcium zirconate, hydroxyapatite, magnesium aluminate, silicon carbide, silicon nitride, strontium ferrite, strontium titanate, titanium carbonitride, titanium carbonitride (7:3), titanium (IV) carbide, zinc titanate, zirconium (IV) silicate, or combinations thereof.

11. The composition according to claim 1 where the nanoparticle is a functionalized metal or metalloid.

12. The composition according to claim 11 where the nanoparticle is (1-mercaptoundec-11-yl)tetra(ethylene glycol) functionalized gold nanoparticles solution, 1-mercapto-(triethylene glycol) methyl ether functionalized gold nanoparticles solution, 3-aminopropyl functionalized silica, 3-aminopropyl-(3-oxobutanoic acid) functionalized silica, decanethiol functionalized silver nanoparticles solution, dodecanethiol functionalized gold nanoparticles solution, dodecanethiol functionalized silver nanoparticles solution, octanethiol functionalized gold nanoparticles solution, and combinations thereof.

13. The composition according to claim 1 where the nanoparticle is a carbon nanoparticle, a diamond nanoparticle, or combinations thereof.

14. The composition according to claim 1 where the nanoparticle has a concentration of from about 2 parts per million to about 20 parts per million.

15. The composition according to claim 1 where the nanoparticle has a concentration of from about 2.5 parts per million to about 15 parts per million.

16. The composition according to claim 2 where the nanoparticle is a metal or metal alloy.

17. The composition according to claim 16 where the nanoparticle is aluminum, copper, copper-zinc alloy, gold, gold colloid solution, a nickel-molybdenum-chromium alloy comprising approximately 55% Ni, 15-17% Mo, 14.5-16.5% Cr, 4-7% Fe and 3-4.5%, iron, iron-nickel alloy, molybdenum, nickel, palladium, platinum, silicon, silver, silver dispersion, silver-copper alloy, silver-platinum alloy, silver-tin alloy, tantalum, tin, titanium, tungsten, zinc, or combinations thereof.

18. The composition according to claim 2 where the nanoparticle is a metal oxide.

19. The composition according to claim 18 where the nanoparticle is aluminum cerium oxide, aluminum oxide, antimony tin oxide, antimony (III) oxide, barium strontium titanium oxide, barium zirconate, bismuth cobalt zinc oxide, bismuth (III) oxide, calcium oxide, cerium (IV) oxide, cerium (IV)-zirconium (IV) oxide, chromium (III) oxide, cobalt aluminum oxide, cobalt (II, III) oxide, copper aluminum oxide, copper iron oxide, copper zinc iron oxide, copper (I) oxide, copper (II) oxide, dysprosium (III) oxide, erbium (III) oxide, europium (III) oxide, gadolinium (III) oxide, holmium (III) oxide, indium tin oxide, indium (III) hydroxide, indium (III) oxide, iron nickel oxide, iron (II, III) oxide, iron (III) oxide, lanthanum (III) oxide, magnesium hydroxide, magnesium oxide, magnetic Iron oxide, neodymium (III) oxide, nickel chromium oxide, nickel cobalt, oxide, nickel zinc, iron oxide, nickel (II) oxide, praseodymium (III, IV) oxide, samarium strontium cobalt oxide, samarium(III) oxide, silica, silicon dioxide, alumina doped, terbium (III, IV) oxide, tin (IV) oxide, titanium silicon oxide, titanium (IV) oxide, titanium (IV) oxide, anatase, titanium (IV) oxide, mixture of rutile and anatase, titanium (IV) oxide, rutile, tungsten (VI) oxide, ytterbium (III) oxide, yttrium aluminum oxide, yttrium iron oxide, yttrium (III) oxide, zinc iron oxide, zinc oxide, zirconium (IV) oxide, zirconium(IV) oxide-yttria stabilized, or combinations thereof.

20. The composition according to claim 18 where the nanoparticle is alumina ($Al_2O_3$), silica ($SiO_2$), titania ($TiO_2$), or combinations thereof.

21. The composition according to claim 2 where the nanoparticle is a ceramic.

22. The composition according to claim 21 where the nanoparticle is aluminum nitride, aluminum titanate, barium ferrite, barium titanate (IV), amorphous calcium phosphate, calcium titanate, calcium zirconate, hydroxyapatite, magnesium aluminate, silicon carbide, silicon nitride, strontium ferrite, strontium titanate, titanium carbonitride, titanium carbonitride (7:3), titanium (IV) carbide, zinc titanate, zirconium (IV) silicate, or combinations thereof.

23. The composition according to claim 2 where the nanoparticle is a functionalized metal or metalloid.

24. The composition according to claim 23 where the nanoparticle is (1-mercaptoundec-11-yl)tetra(ethylene glycol) functionalized gold nanoparticles solution, 1-mercapto-(triethylene glycol) methyl ether functionalized gold nanoparticles solution, 3-aminopropyl functionalized silica, 3-aminopropyl-(3-oxobutanoic acid) functionalized silica, decanethiol functionalized silver nanoparticles solution, dodecanethiol functionalized gold nanoparticles solution, dodecanethiol functionalized silver nanoparticles solution, octanethiol functionalized gold nanoparticles solution, and combinations thereof.

25. The composition according to claim 2 where the nanoparticle is a carbon nanoparticle, a diamond nanoparticle, or combinations thereof.

26. The composition according to claim 2 where the nanoparticle has a concentration of from about 2 parts per million to about 20 parts per million.

27. The composition according to claim 2 where the nanoparticle has a concentration of from about 2.5 parts per million to about 15 parts per million.

28. The composition according to claim 3 where the nanoparticle is a metal or metal alloy.

29. The composition according to claim 28 where the nanoparticle is aluminum, copper, copper-zinc alloy, gold, gold colloid solution, a nickel-molybdenum-chromium alloy comprising approximately 55% Ni, 15-17% Mo, 14.5-16.5% Cr, 4-7% Fe and 3-4.5%, iron, iron-nickel alloy, molybdenum, nickel, palladium, platinum, silicon, silver, silver dispersion, silver-copper alloy, silver-platinum alloy, silver-tin alloy, tantalum, tin, titanium, tungsten, zinc, or combinations thereof.

30. The composition according to claim 3 where the nanoparticle is a metal oxide.

31. The composition according to claim 30 where the nanoparticle is aluminum cerium oxide, aluminum oxide, antimony tin oxide, antimony (III) oxide, barium strontium titanium oxide, barium zirconate, bismuth cobalt zinc oxide, bismuth (III) oxide, calcium oxide, cerium (IV) oxide, cerium (IV)-zirconium (IV) oxide, chromium (III) oxide, cobalt aluminum oxide, cobalt (II, III) oxide, copper aluminum oxide, copper iron oxide, copper zinc iron oxide, copper (I) oxide, copper (II) oxide, dysprosium (III) oxide, erbium (III) oxide, europium (III) oxide, gadolinium (III) oxide, holmium (III) oxide, indium tin oxide, indium (III) hydroxide, indium (III) oxide, iron nickel oxide, iron (II, III) oxide, iron (III) oxide, lanthanum (III) oxide, magnesium hydroxide, magnesium oxide, magnetic Iron oxide, neodymium (III) oxide, nickel chromium oxide, nickel cobalt, oxide, nickel zinc, iron oxide, nickel (II) oxide, praseodymium (III, IV) oxide, samarium strontium cobalt oxide, samarium(III) oxide, silica, silicon dioxide, alumina doped, terbium (III, IV) oxide, tin (IV) oxide, titanium silicon oxide, titanium (IV) oxide, titanium (IV) oxide, anatase, titanium (IV) oxide, mixture of rutile and anatase, titanium (IV) oxide, rutile, tungsten (VI) oxide, ytterbium (III) oxide, yttrium aluminum oxide, yttrium iron oxide, yttrium (III) oxide, zinc iron oxide, zinc oxide, zirconium (IV) oxide, zirconium(IV) oxide-yttria stabilized, or combinations thereof.

32. The composition according to claim 30 where the nanoparticle is alumina ($Al_2O_3$), silica ($SiO_2$), titania ($TiO_2$), or combinations thereof.

33. The composition according to claim 3 where the nanoparticle is a ceramic.

34. The composition according to claim 33 where the nanoparticle is aluminum nitride, aluminum titanate, barium ferrite, barium titanate (IV), amorphous calcium phosphate, calcium titanate, calcium zirconate, hydroxyapatite, magnesium aluminate, silicon carbide, silicon nitride, strontium ferrite, strontium titanate, titanium carbonitride, titanium carbonitride (7:3), titanium (IV) carbide, zinc titanate, zirconium (IV) silicate, or combinations thereof.

35. The composition according to claim 3 where the nanoparticle is a functionalized metal or metalloid.

36. The composition according to claim 35 where the nanoparticle is (1-mercaptoundec-11-yl)tetra(ethylene glycol) functionalized gold nanoparticles solution, 1-mercapto-(triethylene glycol) methyl ether functionalized gold nanoparticles solution, 3-aminopropyl functionalized silica, 3-aminopropyl-(3-oxobutanoic acid) functionalized silica, decanethiol functionalized silver nanoparticles solution, dodecanethiol functionalized gold nanoparticles solution, dodecanethiol functionalized silver nanoparticles solution, octanethiol functionalized gold nanoparticles solution, and combinations thereof.

37. The composition according to claim 3 where the nanoparticle is a carbon nanoparticle, a diamond nanoparticle, or combinations thereof.

38. The composition according to claim 3 where the nanoparticle has a concentration of from about 2 parts per million to about 20 parts per million.

39. The composition according to claim 3 where the nanoparticle has a concentration of from about 2.5 parts per million to about 15 parts per million.

40. A method, comprising:
providing a biological sample;
applying a histochemical process composition to the sample, the composition comprising deionized water, Tris base, boric acid, EDTA disodium dehydrate, a composition comprising 5-chloro-2-methyl-4-isothiazolin-3-one 2.30%, 2-methyl-4-isothiazolin-3-one 0.70%, modified glycol 93-95%, alkyl carboxylate 2-3%, and greater than 0 to about 25 parts per million of at least one nanoparticle; and
performing a histochemical process on the sample.

41. The method according to claim 40 where performing a histochemical process comprises performing cell conditioning on the sample using a cell conditioning composition.

42. The method according to claim 40 where performing a histochemical process includes heating the biological sample and histochemical process composition to a temperature of from about 60° to about 101° C.

43. The method according to claim 40 where the nanoparticle is selected from aluminum, copper, copper-zinc alloy, gold, gold colloid solution, a nickel-molybdenum-chromium alloy comprising approximately 55% Ni, 15-17% Mo, 14.5-16.5% Cr, 4-7% Fe and 3-4.5%, iron, iron-nickel alloy, molybdenum, nickel, palladium, platinum, silicon, silver, silver dispersion, silver-copper alloy, silver-platinum alloy, silver-tin alloy, tantalum, tin, titanium, tungsten, zinc, aluminum cerium oxide, aluminum oxide, antimony tin oxide, antimony (III) oxide, barium strontium titanium oxide, barium zirconate, bismuth cobalt zinc oxide, bismuth (III) oxide, calcium oxide, cerium (IV) oxide, cerium (IV)-zirconium (IV) oxide, chromium (III) oxide, cobalt aluminum oxide, cobalt (II, III) oxide, copper aluminum oxide, copper iron oxide, copper zinc iron oxide, copper (I) oxide, copper (II) oxide, dysprosium (III) oxide, erbium (III) oxide, europium (III) oxide, gadolinium (III) oxide, holmium (III) oxide, indium tin oxide, indium (III) hydroxide, indium (III) oxide, iron nickel oxide, iron (II, III) oxide, iron (III) oxide, lanthanum (III) oxide, magnesium hydroxide, magnesium oxide, magnetic Iron oxide, neodymium (III) oxide, nickel chromium oxide, nickel cobalt, oxide, nickel zinc, iron oxide, nickel (II) oxide, praseodymium (III, IV) oxide, samarium strontium cobalt oxide, samarium(III) oxide, silica, silicon dioxide, alumina doped, terbium (III, IV) oxide, tin (IV) oxide, titanium silicon oxide, titanium (IV) oxide, titanium (IV) oxide, anatase, titanium (IV) oxide, mixture of rutile and anatase, titanium (IV) oxide, rutile, tungsten (VI) oxide, ytterbium (III) oxide, yttrium aluminum oxide, yttrium iron oxide, yttrium (III) oxide, zinc iron oxide, zinc oxide, zirconium (IV) oxide, zirconium(IV) oxide-yttria stabilized, aluminum nitride, aluminum titanate, barium ferrite, barium titanate (IV), amorphous calcium phosphate, calcium titanate, calcium zirconate, hydroxyapatite, magnesium aluminate, silicon carbide, silicon nitride, strontium ferrite, strontium titanate, titanium carbonitride, titanium carbonitride (7:3), titanium (IV) carbide, zinc titanate, zirconium (IV) silicate, (1-mercaptoundec-11-yl)tetra(ethylene glycol) functionalized gold nanoparticles solution, 1-mercapto-(triethylene glycol) methyl ether functionalized gold nanoparticles solution, 3-aminopropyl functionalized silica, 3-aminopropyl-(3-oxobutanoic acid) functionalized silica, decanethiol functionalized silver nanoparticles solution, dodecanethiol functionalized gold nanoparticles solution, dodecanethiol functionalized silver nanoparticles solution, octanethiol functionalized gold nanoparticles solution, a carbon nanoparticle, a diamond nanoparticle, or combinations thereof.

44. The method according to claim 40 where the composition comprises a nanoparticle selected from alumina ($Al_2O_3$), silica ($SiO_2$), titania ($TiO_2$), or combinations thereof.

45. The method according to claim 40 where the composition has a nanoparticle concentration of from about 2 parts per million to about 20 parts per million.

46. The method according to claim 40 where the composition has a nanoparticle concentration of from about 2.5 parts per million to about 15 parts per million.

47. The method according to claim 40 further comprising performing at least one additional histochemical processing step.

48. A method, comprising:
providing a biological sample;
applying a histochemical process composition to the sample, the composition comprising deionized water, sodium citrate dihydrate, citric acid monohydrate, polyoxyethylenesorbitan monolaurate, a composition comprising 5-chloro-2-methyl-4-isothiazolin-3-one 2.30%, 2-methyl-4-isothiazolin-3-one 0.70%, modified glycol 93-95%, alkyl carboxylate 2-3%, and greater than 0 to about 25 parts per million of at least one nanoparticle; and
performing a histochemical process on the sample.

49. The method according to claim 48 where performing a histochemical process comprises performing cell conditioning on the sample using a cell conditioning composition.

50. The method according to claim 48 where performing a histochemical process includes heating the biological sample and histochemical process composition to a temperature of from about 60° to about 101° C.

51. The method according to claim 48 where the nanoparticle is selected from aluminum, copper, copper-zinc alloy, gold, gold colloid solution, a nickel-molybdenum-chromium alloy comprising approximately 55% Ni, 15-17% Mo, 14.5-16.5% Cr, 4-7% Fe and 3-4.5%, iron, iron-nickel alloy, molybdenum, nickel, palladium, platinum, silicon, silver, silver dispersion, silver-copper alloy, silver-platinum alloy, silver-tin alloy, tantalum, tin, titanium, tungsten, zinc, aluminum cerium oxide, aluminum oxide, antimony tin oxide, antimony (III) oxide, barium strontium titanium oxide, barium zirconate, bismuth cobalt zinc oxide, bismuth (III) oxide, calcium oxide, cerium (IV) oxide, cerium (IV)-zirconium (IV) oxide, chromium (III) oxide, cobalt aluminum oxide, cobalt (II, III) oxide, copper aluminum oxide, copper iron oxide, copper zinc iron oxide, copper (I) oxide, copper (II) oxide, dysprosium (III) oxide, erbium (III) oxide, europium (III) oxide, gadolinium (III) oxide, holmium (III) oxide, indium tin oxide, indium (III) hydroxide, indium (III) oxide, iron nickel oxide, iron (II, III) oxide, iron (III) oxide, lanthanum (III) oxide, magnesium hydroxide, magnesium oxide, magnetic Iron oxide, neodymium (III) oxide, nickel chromium oxide, nickel cobalt, oxide, nickel zinc, iron oxide, nickel (II) oxide, praseodymium (III, IV) oxide, samarium strontium cobalt oxide, samarium(III) oxide, silica, silicon dioxide, alumina doped, terbium (III, IV) oxide, tin (IV) oxide, titanium silicon oxide, titanium (IV) oxide, titanium (IV) oxide, anatase, titanium (IV) oxide, mixture of rutile and anatase, titanium (IV) oxide, rutile, tungsten (VI) oxide, ytterbium (III) oxide, yttrium aluminum oxide, yttrium iron oxide, yttrium (III) oxide, zinc iron oxide, zinc oxide, zirconium (IV) oxide, zirconium(IV) oxide-yttria stabilized, aluminum nitride, aluminum titanate, barium ferrite, barium titanate (IV), amorphous calcium phosphate, calcium titanate, calcium zirconate, hydroxyapatite, magnesium aluminate, silicon carbide, silicon nitride, strontium ferrite, strontium titanate, titanium carbonitride, titanium carbonitride (7:3), titanium (IV) carbide, zinc titanate, zirconium (IV) silicate, (1-mercaptoundec-11-yl)tetra(ethylene glycol) functionalized gold nanoparticles solution, 1-mercapto-(triethylene glycol) methyl ether functionalized gold nanoparticles solution, 3-aminopropyl functionalized silica, 3-aminopropyl-(3-oxobutanoic acid) functionalized silica, decanethiol functionalized silver nanoparticles solution, dodecanethiol functionalized gold nanoparticles solution, dodecanethiol functionalized silver nanoparticles solution, octanethiol functionalized gold nanoparticles solution, a carbon nanoparticle, a diamond nanoparticle, or combinations thereof.

52. The method according to claim 48 where the composition comprises a nanoparticle selected from alumina ($Al_2O_3$), silica ($SiO_2$), titania ($TiO_2$), or combinations thereof.

53. The method according to claim 48 where the composition has a nanoparticle concentration of from about 2 parts per million to about 20 parts per million.

54. The method according to claim 48 where the composition has a nanoparticle concentration of from about 2.5 parts per million to about 15 parts per million.

55. The method according to claim 48 further comprising performing at least one additional histochemical processing step.

56. A method, comprising:
providing a biological sample;
applying a histochemical process composition to the sample, the composition comprising deionized water, sodium citrate dihydrate, citric acid monohydrate, 5-chloro-2-methyl-4-isothiazolin-3-one 2.30%, 2-methyl-4-isothiazolin-3-one 0.70%, modified glycol 93-95%, alkyl carboxylate 2-3%, and greater than 0 to about 25 parts per million of at least one nanoparticle; and
performing a histochemical process on the sample.

57. The method according to claim 56 where performing a histochemical process comprises performing cell conditioning on the sample using a cell conditioning composition.

58. The method according to claim 56 where performing a histochemical process includes heating the biological sample and histochemical process composition to a temperature of from about 60° to about 101° C.

59. The method according to claim 56 where the nanoparticle is selected from aluminum, copper, copper-zinc alloy, gold, gold colloid solution, a nickel-molybdenum-chromium alloy comprising approximately 55% Ni, 15-17% Mo, 14.5-16.5% Cr, 4-7% Fe and 3-4.5%, iron, iron-nickel alloy, molybdenum, nickel, palladium, platinum, silicon, silver, silver dispersion, silver-copper alloy, silver-platinum alloy, silver-tin alloy, tantalum, tin, titanium, tungsten, zinc, aluminum cerium oxide, aluminum oxide, antimony tin oxide, antimony (III) oxide, barium strontium titanium oxide, barium zirconate, bismuth cobalt zinc oxide, bismuth (III) oxide, calcium oxide, cerium (IV) oxide, cerium (IV)-zirconium (IV) oxide, chromium (III) oxide, cobalt aluminum oxide, cobalt (II, III) oxide, copper aluminum oxide, copper iron oxide, copper zinc iron oxide, copper (I) oxide, copper (II) oxide, dysprosium (III) oxide, erbium (III) oxide, europium (III) oxide, gadolinium (III) oxide, holmium (III) oxide, indium tin oxide, indium (III) hydroxide, indium (III) oxide, iron nickel oxide, iron (II, III) oxide, iron (III) oxide, lanthanum (III) oxide, magnesium hydroxide, magnesium oxide, magnetic Iron oxide, neodymium (III) oxide, nickel chromium oxide, nickel cobalt, oxide, nickel zinc, iron oxide, nickel (II) oxide, praseodymium (III, IV) oxide, samarium strontium cobalt oxide, samarium(III) oxide, silica, silicon dioxide, alumina doped, terbium (III, IV) oxide, tin (IV) oxide, titanium silicon oxide, titanium (IV) oxide, titanium (IV) oxide, anatase, titanium (IV) oxide, mixture of rutile and anatase, titanium (IV) oxide, rutile, tungsten (VI) oxide, ytterbium (III) oxide, yttrium aluminum oxide, yttrium iron oxide, yttrium (III) oxide, zinc iron oxide, zinc oxide, zirconium (IV) oxide, zirconium(IV) oxide-yttria stabilized, aluminum nitride, aluminum titanate, barium ferrite, barium titanate (IV), amorphous calcium phosphate, calcium titanate, calcium zirconate, hydroxyapatite, magnesium aluminate, silicon carbide, silicon nitride, strontium ferrite, strontium titanate, titanium carbonitride, titanium carbonitride (7:3), titanium (IV) carbide, zinc titanate, zirconium (IV) silicate, (1-mercaptoundec-11-yl)tetra(ethylene glycol) functionalized gold nanoparticles solution, 1-mercapto-(triethylene glycol) methyl ether functionalized gold nanoparticles solution, 3-aminopropyl functionalized silica, 3-aminopropyl-(3-oxobutanoic acid) functionalized silica, decanethiol functionalized silver nanoparticles solution, dodecanethiol functionalized gold nanoparticles solution, dodecanethiol functionalized silver nanoparticles solution, octanethiol functionalized gold nanoparticles solution, a carbon nanoparticle, a diamond nanoparticle, or combinations thereof.

60. The method according to claim 56 where the composition comprises a nanoparticle selected from alumina ($Al_2O_3$), silica ($SiO_2$), titania ($TiO_2$), or combinations thereof.

61. The method according to claim 56 where the composition has a nanoparticle concentration of from about 2 parts per million to about 20 parts per million.

62. The method according to claim 56 where the composition has a nanoparticle concentration of from about 2.5 parts per million to about 15 parts per million.

63. The method according to claim 56 further comprising performing at least one additional histochemical processing step.

* * * * *